(12) United States Patent
Shum et al.

(10) Patent No.: US 12,252,745 B2
(45) Date of Patent: Mar. 18, 2025

(54) DETECTION AND DIGITAL QUANTITATION OF MULTIPLE TARGETS

(71) Applicant: ENUMERIX, INC., Palo Alto, CA (US)

(72) Inventors: Eleen Yee Lam Shum, San Carlos, CA (US); Hei Mun Christina Fan, Palo Alto, CA (US); Stephen P. A. Fodor, Palo Alto, CA (US); Haeun Grace Lee, Palo Alto, CA (US)

(73) Assignee: ENUMERIX, INC., Palo Alto, CA (US)

( * ) Notice: Subject to any disclaimer, the term of this patent is extended or adjusted under 35 U.S.C. 154(b) by 0 days.

(21) Appl. No.: 18/759,368

(22) Filed: Jun. 28, 2024

(65) Prior Publication Data

US 2024/0352523 A1    Oct. 24, 2024

Related U.S. Application Data

(63) Continuation-in-part of application No. 17/939,774, filed on Sep. 7, 2022, now abandoned, which is a continuation of application No. PCT/US2022/042385, filed on Sep. 1, 2022.

(60) Provisional application No. 63/240,164, filed on Sep. 2, 2021.

(51) Int. Cl.
  *C12Q 1/6876* (2018.01)
  *G01N 21/64* (2006.01)
  *G01N 33/542* (2006.01)

(52) U.S. Cl.
  CPC ....... *C12Q 1/6876* (2013.01); *G01N 21/6428* (2013.01); *G01N 33/542* (2013.01); *C12Q 2600/156* (2013.01); *C12Q 2600/16* (2013.01); *G01N 2021/6439* (2013.01)

(58) Field of Classification Search
  CPC ............ C12Q 1/6876; C12Q 2600/156; C12Q 2600/16; G01N 21/6428; G01N 33/542; G01N 2021/6439
  See application file for complete search history.

(56) References Cited

U.S. PATENT DOCUMENTS

| | | |
|---|---|---|
| 2,825,313 A | 3/1958 | Sidney et al. |
| 3,480,616 A | 11/1969 | Osipow et al. |
| 3,644,333 A | 2/1972 | Osipow et al. |
| 4,683,058 A | 7/1987 | Lyman et al. |
| 5,216,033 A | 6/1993 | Pereira et al. |
| 5,707,613 A | 1/1998 | Hill |
| 5,753,241 A | 5/1998 | Ribier et al. |
| 5,925,338 A | 7/1999 | Karassik et al. |
| 6,120,778 A | 9/2000 | Simonnet |
| 6,121,055 A | 9/2000 | Hargreaves |
| 6,329,164 B1 | 12/2001 | Goodwin, Jr. |
| 6,379,682 B1 | 4/2002 | Tchinnis et al. |
| 6,387,357 B1 | 5/2002 | Chopra et al. |
| 6,403,069 B1 | 6/2002 | Chopra et al. |
| 7,041,481 B2 | 5/2006 | Anderson et al. |
| 7,622,076 B2 | 11/2009 | Davies et al. |
| 7,772,287 B2 | 8/2010 | Higuchi et al. |
| RE41,780 E | 9/2010 | Anderson et al. |
| 7,888,017 B2 | 2/2011 | Quake et al. |
| 7,901,939 B2 | 3/2011 | Ismagliov et al. |
| 8,137,912 B2 | 3/2012 | Kapur et al. |
| RE43,365 E | 5/2012 | Anderson et al. |
| 8,658,430 B2 | 2/2014 | Miller et al. |
| 8,765,382 B2 | 7/2014 | Drmanac |
| 8,798,341 B2 | 8/2014 | Baudry et al. |
| 8,871,444 B2 | 10/2014 | Griffiths et al. |
| 8,889,083 B2 | 11/2014 | Ismagilov et al. |
| 8,889,093 B2 | 11/2014 | Malhotra et al. |
| 8,951,939 B2 | 2/2015 | Saxonov et al. |
| 8,968,659 B2 | 3/2015 | Davies et al. |
| 9,012,390 B2 | 4/2015 | Holtze et al. |
| 9,029,083 B2 | 5/2015 | Griffiths et al. |
| 9,039,273 B2 | 5/2015 | Weitz et al. |

(Continued)

FOREIGN PATENT DOCUMENTS

| | | |
|---|---|---|
| CN | 86106153 A | 6/1987 |
| CN | 1089361 A | 7/1994 |

(Continued)

OTHER PUBLICATIONS

Ma et al., Fluorescent Biosensors Based on Single-Molecule Counting, 2016, Acc.chem.Res., 2016,49, 1722-1730 (Year: 2016).*

Shum et al., Post Art; Next-Generation Digital Polymerase Chain Reaction: High-Dynamic-Range Single-Molecule DNA Counting via Ultra-partitioning, Anal. Chem. 2022, 94, 17868-17876 (Year: 2022).*

Chapman, H Glenn et al.: Angular Domain Image Detectability with Changing Turbid Medium Scattering Coefficients. Proc. of SPIE 5695:160-171 (2005).

(Continued)

*Primary Examiner* — Narayan K Bhat
(74) *Attorney, Agent, or Firm* — Wilson Sonsini Goodrich & Rosati

(57) ABSTRACT

This disclosure provides for devices, methods, and systems for performing a non-invasive prenatal testing (NIPT) digital assay upon generating at least a large number of counts per chromosome for a set of chromosomes present in a sample, where performing the NIPT digital assay can include: distributing nucleic acids of the sample and materials for an amplification reaction across a plurality of partitions; amplifying the nucleic acids with the materials, within the plurality of partitions; and generating counts per chromosome upon detecting signals from the plurality of partitions. The inventions enable processing of samples for NIPT digital analyses and/or other digital analyses involving other loci of interest, with unprecedented partitioning, reaction, readout, and analytical performance.

17 Claims, 7 Drawing Sheets

(56) References Cited

U.S. PATENT DOCUMENTS

| | | |
|---|---|---|
| RE45,539 E | 6/2015 | Anderson et al. |
| 9,074,242 B2 | 7/2015 | Larson et al. |
| 9,089,844 B2 | 7/2015 | Hiddessen et al. |
| 9,126,160 B2 | 9/2015 | Ness et al. |
| 9,127,310 B2 | 9/2015 | Larson et al. |
| 9,156,010 B2 | 10/2015 | Colston et al. |
| 9,186,643 B2 | 11/2015 | Griffiths et al. |
| 9,216,392 B2 | 12/2015 | Hindson et al. |
| 9,222,115 B2 | 12/2015 | Marble et al. |
| 9,273,308 B2 | 3/2016 | Link et al. |
| 9,347,095 B2 | 5/2016 | Regan et al. |
| 9,400,242 B2 | 7/2016 | Allano et al. |
| 9,410,151 B2 | 8/2016 | Link et al. |
| 9,441,266 B2 | 9/2016 | Larson et al. |
| 9,446,360 B2 | 9/2016 | Mazutis |
| 9,492,797 B2 | 11/2016 | Makarewicz et al. |
| 9,494,520 B2 | 11/2016 | Link |
| 9,500,664 B2 | 11/2016 | Ness et al. |
| 9,523,116 B2 | 12/2016 | Tzonev et al. |
| 9,556,475 B2 | 1/2017 | Regan et al. |
| RE46,322 E | 2/2017 | Anderson et al. |
| 9,562,837 B2 | 2/2017 | Link |
| 9,567,639 B2 | 2/2017 | Oliphant et al. |
| 9,592,506 B2 | 3/2017 | Ismagilov et al. |
| 9,597,644 B2 | 3/2017 | Davies et al. |
| 9,610,239 B2 | 4/2017 | Feng et al. |
| 9,631,230 B2 | 4/2017 | Davies et al. |
| 9,636,682 B2 | 5/2017 | Hiddessen et al. |
| 9,649,635 B2 | 5/2017 | Hiddessen et al. |
| 9,677,118 B2 | 6/2017 | Zimmermann et al. |
| 9,695,468 B2 | 7/2017 | Hindson et al. |
| 9,708,654 B2 | 7/2017 | Hunicke-Smith et al. |
| 9,745,617 B2 | 8/2017 | Larson et al. |
| 9,764,322 B2 | 9/2017 | Hiddessen et al. |
| 9,788,564 B2 | 10/2017 | Bromley |
| 9,885,643 B2 | 2/2018 | Pautz et al. |
| 9,896,722 B2 | 2/2018 | Link |
| 9,919,277 B2 | 3/2018 | Griffiths et al. |
| 9,925,501 B2 | 3/2018 | Griffiths et al. |
| 9,970,052 B2 | 5/2018 | Do et al. |
| 10,011,865 B2 | 7/2018 | Link |
| RE47,080 E | 10/2018 | Anderson et al. |
| 10,130,950 B2 | 11/2018 | Hung et al. |
| 10,150,786 B2 | 12/2018 | Chia et al. |
| 10,161,007 B2 | 12/2018 | Abate et al. |
| 10,316,873 B2 | 6/2019 | Weitz et al. |
| 10,318,704 B2 | 6/2019 | Chudova et al. |
| 10,428,369 B2 | 10/2019 | Miller et al. |
| 10,508,300 B2 | 12/2019 | Dahl et al. |
| 10,512,910 B2 | 12/2019 | Colston, Jr. et al. |
| 10,537,503 B2 | 1/2020 | Lei et al. |
| 10,604,789 B2 | 3/2020 | Regan et al. |
| 10,619,192 B2 | 4/2020 | Chiu et al. |
| 10,622,094 B2 | 4/2020 | Kim et al. |
| 10,626,451 B2 | 4/2020 | Davies et al. |
| 10,639,598 B2 | 5/2020 | Griffiths et al. |
| 10,676,786 B2 | 6/2020 | Davies et al. |
| 10,745,762 B2 | 8/2020 | Abate et al. |
| 10,748,290 B2 | 8/2020 | Adiga |
| 10,927,407 B2 | 2/2021 | Link |
| 10,967,338 B2 | 4/2021 | Davies et al. |
| 11,001,896 B2 | 5/2021 | Abate et al. |
| 11,084,039 B2 | 8/2021 | Davies et al. |
| 11,085,070 B2 | 8/2021 | Regan et al. |
| 11,130,128 B2 | 9/2021 | Ness et al. |
| RE48,788 E | 10/2021 | Anderson et al. |
| 11,162,136 B1 | 11/2021 | Fan et al. |
| 11,199,532 B2 | 12/2021 | Handique et al. |
| 11,203,787 B2 | 12/2021 | Abate et al. |
| 11,242,558 B2 | 2/2022 | Fan et al. |
| 11,254,968 B2 | 2/2022 | Larson et al. |
| 11,278,898 B2 | 3/2022 | Ismagilov et al. |
| 11,447,817 B2 | 9/2022 | Fan et al. |
| 11,494,914 B2 | 11/2022 | Adiga |
| 11,542,546 B2 | 1/2023 | Fan et al. |
| 11,650,404 B2 | 5/2023 | Meyer et al. |
| 11,814,619 B2 | 11/2023 | Shum et al. |
| 12,000,842 B2 | 6/2024 | Fan et al. |
| 2004/0081633 A1 | 4/2004 | Mercier et al. |
| 2005/0164241 A1 | 7/2005 | Hahn et al. |
| 2006/0128883 A1 | 6/2006 | Garrison et al. |
| 2008/0070792 A1 | 3/2008 | Stoughton et al. |
| 2008/0182910 A1 | 7/2008 | Qiu et al. |
| 2009/0029377 A1 | 1/2009 | Lo et al. |
| 2009/0239308 A1 | 9/2009 | Dube et al. |
| 2010/0173394 A1 | 7/2010 | Colston, Jr. et al. |
| 2011/0033862 A1 | 2/2011 | Rabinowitz et al. |
| 2012/0015842 A1 | 1/2012 | Scholl et al. |
| 2012/0258516 A1 | 10/2012 | Schultz et al. |
| 2012/0322058 A1 | 12/2012 | Regan et al. |
| 2014/0272996 A1 | 9/2014 | Bemis |
| 2015/0031034 A1 | 1/2015 | Hindson et al. |
| 2015/0307919 A1 | 10/2015 | Ness et al. |
| 2017/0051355 A1 | 2/2017 | Zimmermann et al. |
| 2018/0092847 A1 | 4/2018 | Schutt et al. |
| 2018/0136114 A1 | 5/2018 | Delattre et al. |
| 2018/0251817 A1 | 9/2018 | Do et al. |
| 2019/0255531 A1 | 8/2019 | Hindson et al. |
| 2019/0358625 A1 | 11/2019 | Huang et al. |
| 2019/0360020 A1 | 11/2019 | Huang et al. |
| 2020/0002748 A1 | 1/2020 | Miller et al. |
| 2020/0010876 A1 | 1/2020 | MacDonald et al. |
| 2020/0037638 A1 | 2/2020 | Faraci et al. |
| 2020/0254400 A1 | 8/2020 | Griffiths et al. |
| 2020/0354772 A1 | 11/2020 | Davies et al. |
| 2020/0360928 A1 | 11/2020 | Ismagilov et al. |
| 2021/0254147 A1 | 8/2021 | MacDonald et al. |
| 2021/0262020 A1 | 8/2021 | Link |
| 2021/0349027 A1 | 11/2021 | Fei et al. |
| 2021/0388426 A1 | 12/2021 | Wang et al. |
| 2021/0388446 A1 | 12/2021 | Abate et al. |
| 2022/0008914 A1 | 1/2022 | Hiddessen et al. |
| 2022/0040701 A1 | 2/2022 | Davies et al. |
| 2022/0170085 A1 | 6/2022 | Fan et al. |
| 2022/0178939 A1 | 6/2022 | Anekella et al. |
| 2022/0186308 A1 | 6/2022 | Fan et al. |
| 2022/0213530 A1 | 7/2022 | Larson et al. |
| 2022/0280941 A1 | 9/2022 | Fan et al. |
| 2022/0283174 A1 | 9/2022 | Fan et al. |
| 2022/0339620 A1 | 10/2022 | Huang et al. |
| 2022/0355292 A1 | 11/2022 | Hindson et al. |
| 2022/0362764 A1 | 11/2022 | Hindson et al. |
| 2022/0389410 A1 | 12/2022 | Shum et al. |
| 2022/0411857 A1 | 12/2022 | Fan et al. |
| 2023/0029710 A1 | 2/2023 | Lai et al. |
| 2023/0057343 A1 | 2/2023 | Do et al. |
| 2023/0074085 A1 | 3/2023 | Shum et al. |
| 2023/0086845 A1 | 3/2023 | Larson et al. |
| 2023/0100349 A1 | 3/2023 | Fei et al. |
| 2023/0193385 A1 | 6/2023 | Shum et al. |
| 2023/0212561 A1 | 7/2023 | Shum et al. |
| 2023/0220447 A1 | 7/2023 | Samuels et al. |
| 2023/0287482 A1 | 9/2023 | Fan et al. |

FOREIGN PATENT DOCUMENTS

| | | |
|---|---|---|
| CN | 2612943 Y | 4/2004 |
| CN | 1758405 A | 4/2006 |
| CN | 101904802 A | 12/2010 |
| CN | 103145346 A | 6/2013 |
| CN | 103649813 A | 3/2014 |
| CN | 104111242 A | 10/2014 |
| CN | 104237186 A | 12/2014 |
| CN | 104284970 A | 1/2015 |
| CN | 104407436 A | 3/2015 |
| CN | 104630202 A | 5/2015 |
| CN | 104741156 A | 7/2015 |
| CN | 104741158 A | 7/2015 |
| CN | 104815709 A | 8/2015 |
| CN | 104846100 A | 8/2015 |
| CN | 105854965 A | 8/2016 |
| CN | 106053346 A | 10/2016 |
| CN | 106076443 A | 11/2016 |
| CN | 106459585 A | 2/2017 |

(56) References Cited

FOREIGN PATENT DOCUMENTS

| | | |
|---|---|---|
| CN | 107119145 A | 9/2017 |
| CN | 207062288 U | 3/2018 |
| CN | 108135813 A | 6/2018 |
| CN | 109060736 A | 12/2018 |
| CN | 109234363 A | 1/2019 |
| EP | 2534267 A2 | 12/2012 |
| EP | 2534267 B1 | 4/2018 |
| EP | 2825313 B1 | 5/2018 |
| EP | 3033445 B1 | 1/2020 |
| EP | 2970668 B1 | 7/2020 |
| EP | 3417941 B1 | 3/2022 |
| JP | 3568846 B2 | 9/2004 |
| WO | WO-2008079274 A1 | 7/2008 |
| WO | WO-2009149449 A1 | 12/2009 |
| WO | WO-2015097185 A1 | 7/2015 |
| WO | WO-2017215428 A1 | 12/2017 |
| WO | WO-2017215429 A1 | 12/2017 |
| WO | WO-2018013691 A1 | 1/2018 |
| WO | WO-2020001529 A1 | 1/2020 |
| WO | WO-2020010137 A1 | 1/2020 |
| WO | WO-2020037113 A1 | 2/2020 |
| WO | WO-2020037130 A1 | 2/2020 |
| WO | WO-2020061524 A1 | 3/2020 |
| WO | WO-2020078466 A1 | 4/2020 |
| WO | WO-2021046135 A1 | 3/2021 |
| WO | WO-2021119201 A1 | 6/2021 |
| WO | WO-2021119202 A1 | 6/2021 |
| WO | WO-2022187684 A1 | 9/2022 |
| WO | WO-2022256612 A1 | 12/2022 |
| WO | WO-2023034531 A1 | 3/2023 |
| WO | WO-2023122041 A1 | 6/2023 |
| WO | WO-2023133094 A1 | 7/2023 |
| WO | WO-2023172977 A1 | 9/2023 |

OTHER PUBLICATIONS

Dai et al.: A dPCR-NIPT assay for detections of trisomies 21, 18 and 13 in a single-tube reaction-could it replace serum biochemical tests as a primary maternal plasma screening tool?. Journal of Translational Medicine 20:269 (2022). https://doi.org/10.1186/s12967-022-03455-y.
Engelbrecht, Christoph J. et al.: Miniaturized selective plane illumination microscopy for high-contrast in vivo fluorescence imaging. Opt Lett. 35(9):1413-5 (2010). doi: 10.1364/OL.35.001413.
EP21787733.1 Extended European Search Report dated Apr. 25, 2024.
Huang et al.: Centrifugal micro-channel array droplet generation for highly parallel digital PCR. Lap on a Chip 17(2):235-240 (2017).
Jacky et al.: Virtual-Partition Digital PCR for High-Precision Chromosomal Counting Applications. Anal. Chem. 93(51):17020-17029 (2021). bioRxiv reprinted doi: https://doi.org/10.1101/2021.04.29.441975.
Jiang, Hao, et al. Droplet-based light-sheet fluorescence microscopy for high-throughput sample preparation, 3-D imaging and quantitative analysis on a chip. Lab Chip 17(13):2193-2197 (2017).
Liao et al.: Combination of fluorescence color and melting temperature as a two-dimensional label for homogeneous multiplex PCR detection. Nucleic Acids Research 2013, 41:7 e76 (2013).
Liao; Peiyu et al.: Three-dimensional digital PCR through light-sheet imaging of optically cleared emulsion. PNAS 117(41):25628-25633 (2020). https://doi.org/10.1073/pnas.200244811.
McMahon et al.: Multiplexed Single Intact Cell Droplet Digital PCR (Music ddPCR) Method for Specific Detection of Enterohemorrhagic E. coli (EHEC) in Food Enrichment Cultures. Frontiers in Microbiology 8:332 (2017).
PCT/CN2017/085891 International Search Report and Written Opinion dated Sep. 1, 2017.
PCT/CN2017/085892 International Search Report and Written Opinion dated Aug. 11, 2017.
PCT/CN2019/093241 International Search Report and Written Opinion dated Oct. 8, 2019.
PCT/CN2019/111938 International Search Report and Written Opinion dated Jan. 16, 2020.
PCT/US2021/027353 International Search Report and Written Opinion dated Aug. 13, 2021.
PCT/US2022/018994 (WO2022187684) International Search Report and Written Opinion dated Jun. 30, 2022.
PCTUS2022042385 International Search Report and Written Opinion dated Dec. 8, 2022.
Saghafi; Saiedeh et al.: Recent development in light Ultramicroscopy using aspherical optical elements. SPIE Optical Systems Design, vol. 8550, 85500K (2012) (abstract).
Schulman et al.: Formation of microemulsions by amino alkyl alcohols. Ann N Y Acad Sci. 92:366-371 doi:10.1111/j.1749-6632.1961.tb44987.x (1961).
Shum et al.: Next-Generation Digital Polymerase Chain Reaction: High-Dynamic-Range Single-Molecule DNA Counting via Ultrapartitioning. Anal. Chem. 94(51):17868-17876 (2022).
Tan et al.: A multiplex droplet digital PCR assay for non-invasive prenatal testing of fetal aneuploidies. Analyst 144:2239-2247 (2019). DOI: https://doi.org/10.1039/C8AN02018C.
U.S. Appl. No. 17/687,080 Office Action dated Jul. 16, 2024.
U.S. Appl. No. 17/687,080 Office Action dated Mar. 14, 2024.
U.S. Appl. No. 17/711,417 Notice of Allowance dated Feb. 21, 2024.
U.S. Appl. No. 17/711,417 Office Action dated Jul. 7, 2023.
U.S. Appl. No. 17/939,774 Office Action dated Feb. 14, 2024.
Vladisavljević et al.: Production of uniform droplets using membrane, microchannel and microfluidic emulsification devices. Microfluidics and Nanofluidics 13:151-178 (2012).
Wright et al.: The use of cell-free fetal nucleic acids in maternal blood for non-invasive prenatal diagnosis. Human Reproduction Update 15(1):139-151 (2009).
Yamashita et al.: Generation of monodisperse cell-sized microdroplets using a centrifuge-based axisymmetric co-flowing microfluidic device. Journal of Bioscience and Bioengineering 119(4): 492-495 (2014).
Yanny et al.: Miniscope3D: optimized single-shot miniature 3D fluorescence microscopy. Light: Science & Applications 9:171 (2020).
Zhao et al.: Massive droplet generation for digital PCR via a smart step emulsification chip integrated in a reaction tub. Analyst 2021, 146:15568 (2021).
Zhu et al., Highly sensitive and quantitative detection of rare pathogens through agarose droplet microfluidic emulsion PCR at the single-cell level. Lab on a Chip 12(20):3907-3913 (2012).
EP21787733.1 European Extend Search dated Apr. 25, 2024.
Office Action dated Feb. 14, 2024 issued in U.S. Appl. No. 17/939,774.

* cited by examiner

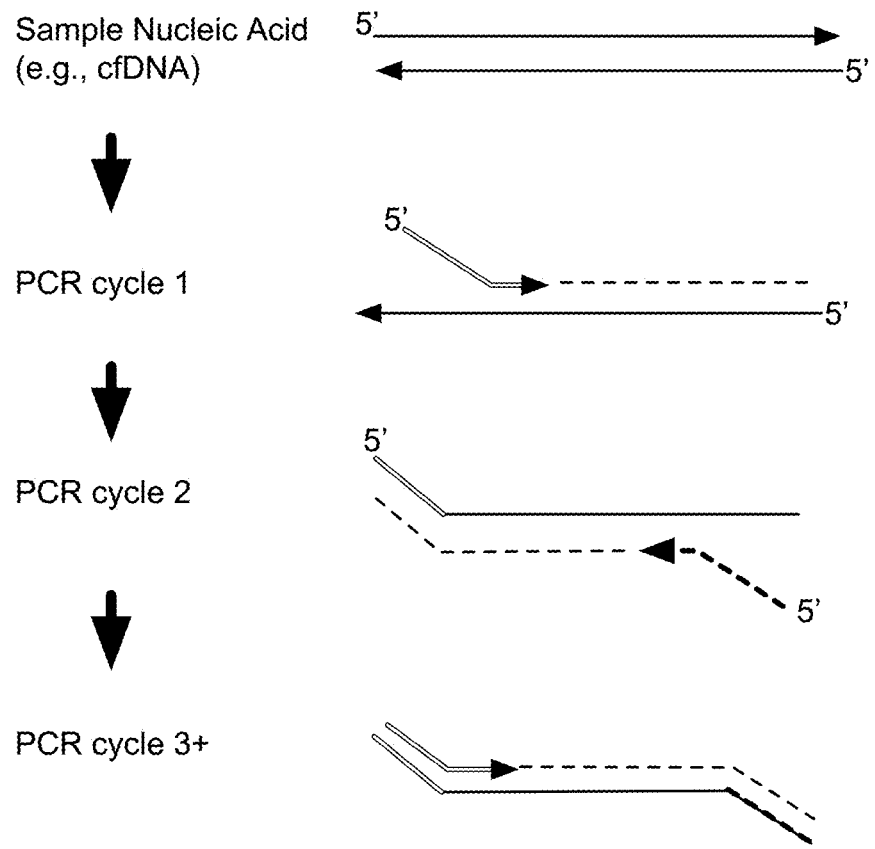

Multiplex amplification mediated by primer sets that target multiple loci (1-plex = 1 primer pair = 1 loci). Black arrows indicate loci-specific recognition sequence.

Each forward/reverse primer contains an adapter sequence.

The adapters increase the specificity of primer binding after multiple cycles.

Multiplex primers all flank a target specific probe. Each probe encodes for a different target

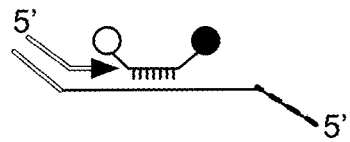

FIGURE 3

DETECTION AND DIGITAL QUANTITATION OF MULTIPLE TARGETS

CROSS-REFERENCE

This application is a continuation in part of U.S. patent application Ser. No. 18/481,950, filed Oct. 5, 2023, which is a continuation of U.S. patent application Ser. No. 18/085,217, filed Dec. 20, 2022, now U.S. Pat. No. 11,834,714, issued Dec. 5, 2023, which is a continuation of International Patent Application No. PCT/US2022/053413, filed Dec. 19, 2022, which claims the benefit of U.S. Provisional Application No. 63/291,813, filed Dec. 20, 2021, each of which applications is incorporated in its entirety herein by this reference.

TECHNICAL FIELD

The disclosure generally relates to prenatal testing, screening, and diagnostics.

BACKGROUND OF THE INVENTION

The discovery of fetal material (e.g., cell-free DNA (cfDNA)) circulating in maternal blood and the application of high order counting technologies enabled non-invasive prenatal testing (NIPT) for various indications. In particular, fetal aneuploidy screening is one of the most common forms of prenatal diagnostics. Traditionally, the diagnosis is performed using methods such as chorionic villus sampling or amniocentesis, in order to detect fetal aneuploidy by counting chromosomal copies. Current fetal aneuploidy screening is often performed via next-generation sequencing (NGS) or microarrays, which involve complex multi-day workflows using expensive equipment. In more detail, NGS and microarrays are commonly used for NIPT because of the ability of such technologies to discern minute fetal chromosomal count differences from cell free DNA (cfDNA) in maternal blood. Since NGS requires significant infrastructure investment and maintenance, NIPT screening is currently confined to a handful of centralized clinical core laboratories, and such a model often contributes to delays in medical decision making.

Due to the state of the technologies, NIPT and associated diagnostic approaches are typically cost-ineffective, low resolution, and/or resource-intensive (especially in the context of multiplexed testing), as evidenced by performance primarily by centralized laboratories.

As such, there is a need for innovation in fields relating to prenatal testing, screening, and diagnostics.

SUMMARY OF THE INVENTION

Currently, platforms and methods for performing NIPT involve significant infrastructure investment and maintenance (e.g., in the context of next generation sequencing), thereby confining NIPT screening to a handful of centralized clinical core laboratories. Such a model can limit access, produce long turnaround times, and contribute to delays in medical decision making. Furthermore, current standard testing solutions are typically cost-ineffective, low resolution, and/or resource-intensive, as evidenced by performance primarily by centralized laboratories.

Accordingly, this disclosure describes embodiments, variations, and examples of systems, methods, and compositions for breaking requirements around NIPT in a high-performance and efficient manner, and with less complex instrumentation.

An aspect of the disclosure provides compositions, methods, and systems for implementation of highly multiplexed molecular diagnostic assays for NIPT, other prenatal tests, and other sample characterization techniques. In specific examples, aspects of the present disclosure can be used to detect various trisomies and/or other aneuploidies in a multiplexed manner. In examples, the compositions, methods, and systems can involve testing for aneuploidies in chromosome 13, chromosome 18, and/or chromosome 21. In other examples, the compositions, methods, and systems can involve testing or characterization of aneuploidies or other genetic disorders in other chromosomes. In specific examples, aspects of the present disclosure can be used to target genomic diseases, associated with but not limited to one or more locis associated with: chromosome 21, chromosome 18, chromosome 13, chromosome X, chromosome Y, 22q11.2 deletion/DiGeorge's Syndrome, Down syndrome, Klinefelter syndrome, XYY syndrome, Turner syndrome, deletion syndromes, other chromosomal abnormalities, rare mutation detection, minimal residual disease, and/or other diseases.

An aspect of the disclosure provides compositions, methods, and systems for generation of chromosomal counts and differential chromosomal count ratios across different fetal fraction scenarios. In particular, due to the relatively low fetal fraction in maternal cell free DNA, a higher order level of DNA counting is required for accurate determination and in order to achieve suitable statistical confidence to distinguish between non-aneuploid and aneuploid fetuses. Current approaches for NIPT rely on platforms such as next generation sequencing (NGS) and microarrays, which are expensive with complex multi-day workflows, limiting its deployment in typical hospital laboratories. On the other hand, platforms such as digital PCR, while being a gold standard analytical platform, is at least an order of magnitude away in relation to generating levels of count suitable for diagnosis. Furthermore, other digital PCR platforms suffer from low precision due low partitioning capabilities, and rely upon Poisson correction factors. Aspects of the present disclosure include digital assay technologies that far exceed the precision of standard digital PCR platforms, and can perform at a DNA counting range akin to NGS, which makes digital ultraPCR suitable for NIPT. Example results include production of high counts (e.g., from a 10 mL sample, from a smaller than 10 mL sample, from a larger than 10 mL sample) required for NIPT fetal aneuploidy screening.

In examples, the systems, methods, and compositions described can be used to enable counting of greater than n counts, with partitioning performed in a manner such that that the occupancy per template remains in the single molecule regime. Thus, there is minimal or no overlap between different template molecules with individual partitions and no statistical correction is needed (e.g., due to non-existent partitioning error). This allows the systems, methods, and compositions to enable measurement performance down to at least a 2% difference in counts (e.g., where a 2% difference in counts is equivalent to a 4% fetal fraction from fetus with trisomy or monosomy). In examples, n 50,000 counts per chromosome for each of a set of chromosomes of interest, 60,000 counts per chromosome for each of a set of chromosomes of interest, 70,000 counts per chromosome for each of a set of chromosomes of interest, 80,000 counts per chromosome for each of a set of chromosomes of interest, 90,000 counts per chromosome for each of a set of chromosomes of interest, 100,000 counts per chromosome for each of a set of chromosomes of interest, 120,000 counts per chromosome for each of a set of chromosomes of interest, 130,000 counts per chromosome for each of a set of chromosomes of interest, 140,000 counts per chromosome for each of a set of chromosomes of interest, 150,000 counts per chromosome for each of a set of chromosomes of interest, 160,000 counts per chromosome for each of a set of chromosomes of interest, 170,000 counts per chromosome for each of a set of chromosomes of interest, 180,000 counts per chromosome for each of a set of chromosomes of interest, 190,000 counts per chromosome for each of a set of chromosomes of interest, 200,000 counts per chromosome for each of a set of chromosomes of interest, 210,000 counts per chromosome for each of a set of chromosomes of interest, 220,000 counts per chromosome for each of a set of chromosomes of interest, 230,000 counts per chromosome for each of a set of chromosomes of interest, 240,000 counts per chromosome for each of a set of chromosomes of interest, 250,000 counts per chromosome for each of a set of chromosomes of interest, 260,000 counts per chromosome for each of a set of chromosomes of interest, 270,000 counts per chromosome for each of a set of chromosomes of interest, 280,000 counts per chromosome for each of a set of chromosomes of interest, 290,000 counts per chromosome for each of a set of chromosomes of interest, 300,000 counts per chromosome for each of a set of chromosomes of interest, or even other counts per chromosome for each of a set of chromosomes of interest.

In examples, the systems, methods, and compositions described can be used to generate, from a partitioned sample, greater than 50,000 counts per chromosome for each of a set of chromosomes of interest, greater than 60,000 counts per chromosome for each of a set of chromosomes of interest, greater than 70,000 counts per chromosome for each of a set of chromosomes of interest, greater than 80,000 counts per chromosome for each of a set of chromosomes of interest, greater than 90,000 counts per chromosome for each of a set of chromosomes of interest, greater than 100,000 counts per chromosome for each of a set of chromosomes of interest, greater than 120,000 counts per chromosome for each of a set of chromosomes of interest, greater than 130,000 counts per chromosome for each of a set of chromosomes of interest, greater than 140,000 counts per chromosome for each of a set of chromosomes of interest, greater than 150,000 counts per chromosome for each of a set of chromosomes of interest, greater than 160,000 counts per chromosome for each of a set of chromosomes of interest, greater than 170,000 counts per chromosome for each of a set of chromosomes of interest, greater than 180,000 counts per chromosome for each of a set of chromosomes of interest, greater than 190,000 counts per chromosome for each of a set of chromosomes of interest, greater than 200,000 counts per chromosome for each of a set of chromosomes of interest, greater than 210,000 counts per chromosome for each of a set of chromosomes of interest, greater than 220,000 counts per chromosome for each of a set of chromosomes of interest, greater than 230,000 counts per chromosome for each of a set of chromosomes of interest, greater than 240,000 counts per chromosome for each of a set of chromosomes of interest, greater than 250,000 counts per chromosome for each of a set of chromosomes of interest, greater than 260,000 counts per chromosome for each of a set of chromosomes of interest, greater than 270,000 counts per chromosome for each of a set of chromosomes of interest, greater than 280,000 counts per chromosome for each of a set of chromosomes of interest, greater than 290,000 counts per chromosome for each of a set of chromosomes of interest, greater than 300,000 counts per chromosome for each of a set of chromosomes of interest, or even greater counts per chromosome for each of a set of chromosomes of interest.

In the context of NIPT assays, maternal samples processed using compositions, according to the methods, and/or by systems described can have a fetal fraction (FF) less than 15%, less than 14%, less than 13%, less than 12%, less than 11%, less than 10%, less than 9%, less than 8%, less than 7%, less than 6%, less than 5%, less than 4%, less than 3%, or less than 2%. Percentages described are for samples without enrichment of a maternal sample by spiked-in fetal genetic material (e.g., without enrichment of fetal nucleic acid material in the sample).

Aspects of the present disclosure also confer(s) the benefit of involving multiplexed primers structured to flank chromosome-specific probes that encode for different chromosomes. Multiplexed primer compositions can be configured for 20-plex amplification of loci of interest for each chromosome of a set of chromosomes being analyzed, 30-plex amplification of loci of interest for each chromosome of a set of chromosomes being analyzed, 40-plex amplification of loci of interest for each chromosome of a set of chromosomes being analyzed, 50-plex amplification of loci of interest for each chromosome of a set of chromosomes being analyzed, 60-plex amplification of loci of interest for each chromosome of a set of chromosomes being analyzed, 70-plex amplification of loci of interest for each chromosome of a set of chromosomes being analyzed, 80-plex amplification of loci of interest for each chromosome of a set of chromosomes being analyzed, 90-plex amplification of loci of interest for each chromosome of a set of chromosomes being analyzed, 100-plex amplification of loci of interest for each chromosome of a set of chromosomes being analyzed, or greater.

In particular, successful multiplexing at this level is attributed to the high degree of partitioning (with achievable numbers of generated partitions described) and extremely low occupancy (with achievable percent occupancies described), such that multiple molecules from the target molecules of interest (e.g., greater than 200 targets) have a minimal (or zero) probability of occupying the same partition as another target molecule. In such a high-partition and low-occupancy regime, there is no competition associated with multiple target molecules per partition, and the platform is not subject to problems related to differences in PCR efficiency between different target molecules.

As such, the disclosure provides compositions, systems, and methods for digital assays (e.g., NIPT digital assays) that are at least 90-plex, 100-plex, 110-plex, 120-plex, 130-plex, 140-plex, 150-plex, 160-plex, 170-plex, 180-plex, 190-plex, 200-plex, 210-plex, 220-plex, 230-plex, 240-plex, 250-plex, 260-plex, 270-plex, 280-plex, 290-plex, 300-plex, or greater. The set of chromosomes being analyzed can include 2 chromosomes, 3 chromosomes, 4 chromosomes, 5 chromosomes, 6 chromosomes, 7 chromosomes, 8 chromosomes, 9 chromosomes, 10 chromosomes, or greater.

The disclosure also provides oligonucleotide compositions and designs for multiplexed assays (e.g., locked nucleic acid (LNA) assays, Taqman assays, etc.). Such improved oligonucleotides improve sample processing, with respect to primer cleanup/removal, reduction of background, implementation of compatible forward and reverse primers for direct multiplexed assays (e.g., PCR), implementation of checks for complementarity of amplicons to non-self probes (i.e., in both sense and antisense strands), implementation of checks for complementarity of primers to probes (i.e., in both sense and antisense strands), generation of positive and negative controls for a clinical workflow, establishment of limits of detection (LoDs) and other metrics for NIPT ultraPCR assays, and/or other improvements.

The disclosure also provides systems, methods, and compositions for a cost-effective and high resolution end-point droplet digital PCR platform that allows for DNA counting of millions of DNA targets, in a manner that can be performed with and without complex workflows such as NGS. Furthermore, aspects of the present disclosure produce a paradigm shift by encouraging widespread implementation of NIPT in decentralized laboratories around the world, by providing mechanisms for low-cost, high resolution NIPT. These aspects thus have the ability to democratize NIPT by introducing a simple, yet high resolution, platform to allow NIPT and other testing to be performed in local laboratories at significantly lower cost (e.g., ~100 times lower cost). By doing this, expectant parents and healthcare providers can receive accurate NIPT results more efficiently and at significantly reduced cost, leading to better test accessibility and avoiding delay of medical decisions.

The disclosure further provides non-naturally occurring compositions for facilitating assessment of biological material, amplification of nucleic acid material from isolated biological materials, constructing sequencing libraries, and sequencing nucleic acid material for characterization of said biological material. In particular, the systems, methods, and compositions are useful in achieving digital DNA counting at a scale akin to NGS in a single day workflow, and without NGS-like investments in time, instrumentation, and costs. The systems and methods described involve ultra-partitioning using centrifugation to generate partitions at an unprecedented rate, followed by counting DNA-positive droplets after amplification.

Relatedly, an aspect of the disclosure provides embodiments, variations, and examples of devices and methods for rapidly generating partitions (e.g., droplets from a sample fluid, droplets of an emulsion) and distributing nucleic acid material (e.g., for NIPT) across partitions, where, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid (e.g., a mixture of nucleic acids of the sample and materials for an amplification reaction), where application of a force to the device or sample fluid generates a plurality of droplets within the collecting container at an extremely high rate (e.g., of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, of at least 4 million droplets/minute, of at least 5 million droplets/minute, of at least 6 million droplets per minute, etc.), where the droplets are stabilized in position (e.g., in a close-packed format, in equilibrium stationary positions) within the collecting container.

An aspect of the disclosure provides embodiments, variations, and examples of a method for rapidly generating partitions (e.g., droplets from a sample fluid, droplets of an emulsion) within a collecting container at an extremely high rate, each of the plurality of droplets including an aqueous mixture for a digital analysis, wherein upon generation, the plurality of droplets is stabilized in position (e.g., in a close-packed format, at equilibrium stationary positions, etc.) within a continuous phase (e.g., as an emulsion having a bulk morphology defined by the collecting container). In aspects, partition generation can be executed by driving the sample fluid through a distribution of holes of a membrane, where the applied force can be one or more of centrifugal (e.g., under centrifugal force), associated with applied pressure, magnetic, or otherwise physically applied.

In relation to a single-tube workflow in which the collecting container remains closed (e.g., the collecting container has no outlet, there is no flow out of the collecting container, to avoid sample contamination), method(s) can further include transmitting heat to and from the plurality of droplets within the closed collecting container according to an assay protocol. In relation to generation of emulsions having suitable clarity (e.g., with or without refractive index matching), method(s) can further include transmission of signals from individual droplets from within the closed collecting container, for readout (e.g., by an optical detection platform, by another suitable detection platform).

Where method(s) include transmitting heat to and from the plurality of droplets, within the closed container, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

Examples of partition generation methods can include generating an extremely high number of droplets (e.g., greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-30 micrometers, etc.) that is relevant for digital analyses, target detection, individual molecule partitioning, or other applications.

In relation to ultra-partitioning, the disclosure provides methods for partitioning in a manner that satisfies minimum DNA counting requirements for NIPT, with a 5-log dynamic range, with a 6-log dynamic range, or with a higher dynamic range.

In examples, the approach discussed is designed around a simple workflow to enable deployment to local and decentralized laboratories. First, samples are carried end-to-end in the same PCR tube for user convenience and to minimize sample contamination. Second, ultra-partitioning and PCR amplification can be performed in standard laboratory equipment such as a swing bucket centrifuge and thermal cycler, lowering the infrastructure cost for ultraPCR adoption. However, compositions of the disclosure can also be utilized in coordination with various technologies for isolating material in single-molecule format (e.g., by use of wells, by use of droplets, by use of other partitioning elements, etc.).

The disclosure generally provides mechanisms for efficient capture and labeling of target material (e.g., DNA, RNA, miRNA, proteins, small molecules, single analytes, multianalytes, etc.) in order to enable genomic, proteomic, and/or other multi-omic characterization of materials for various applications.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

Furthermore, where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

BRIEF DESCRIPTION OF THE DRAWINGS

FIG. 3 depicts an example multiplexed amplification process associated with an NIPT assay or other assay.

DETAILED DESCRIPTION OF THE INVENTION(S)

Figure 1A:
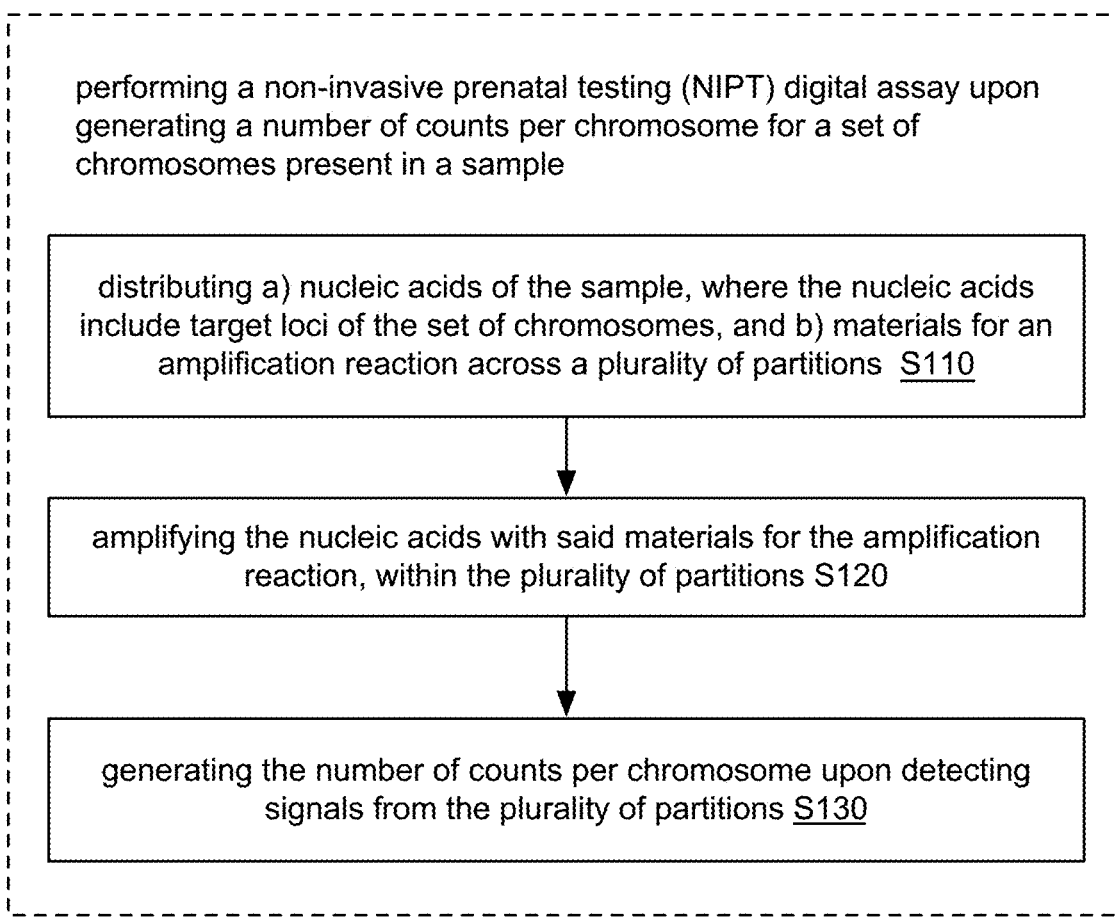
FIG. 1A depicts a flowchart of an embodiment of a method for performance of a digital NIPT assay.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. General Overview

In particular, the systems, methods, and compositions of the present disclosure enable detection and digital quantitation of a set of targets having a number much greater than the number of channels (e.g., color channels, fluorescence detection channels) available for detection. Multiplexed detection involving a greater number of targets than available color channels for detection is based upon one or more of: color combinatorics, stimulus-responsive probes, tandem probes, conjugated polymer probes, and other mechanisms for increasing the number of targets that can be simultaneously detected in a digital assay. Such functionality is attributed to operation in a regime involving low occupancy of a large number of partitions, such that there is an extremely low probability of overlap between target template molecules within individual partitions. Large partition numbers contribute to significantly low percentages of doublets (e.g., single partitions occupied by two targets), triplets (e.g., single partitions occupied by three targets), or other forms of multi-plets (single partitions occupied by multiple targets). As such, signals from different amplified target templates distributed across individual partitions can be differentially detected and analyzed in relation to performance of digital assays.

In the context of emulsion digital PCR with partitions retained in bulk within a container, the systems, methods, and compositions of the present disclosure achieve improved signal-to-noise (SNR) with respect to detection of signals from a partition surrounded in three dimensions by other partitions also potentially emitting signals, where the partitions are interrogated by a three dimensional imaging technique. Some assay chemistries (e.g., such as EvaGreen chemistry, SYBR chemistry) are less appropriate for such applications as they can yield high levels of background noise that reduce assay performance.

In the context of digital multiplexed analyses, the disclosure also provides systems, methods, and compositions that can achieve a high dynamic range, due to the number of partitions involved and occupancy of the partitions by targets of the sample. In examples, the systems, methods, and compositions can provide a dynamic range of: over 4 orders of magnitude from a lower count capability to a higher count capability (e.g., at least $10^4$), over 5 orders of magnitude from a lower count capability to a higher count capability (e.g., at least $10^5$), over 6 orders of magnitude from a lower count capability to a higher count capability (e.g., at least $10^6$), over 7 orders of magnitude from a lower count capability to a higher count capability (e.g., at least $10^7$), or greater, for sample volumes described. In examples, the systems, methods, and compositions can achieve quantification of targets over a 4-log dynamic range, over a 5-log dynamic range, over a 6-log dynamic range, over a 7-log dynamic range, or greater, for sample volumes described.

For partitions arranged in bulk (e.g., in close-packed format, in the form of an emulsion) within a closed container, the systems, methods. and compositions described can provide discernable signals from individual partitions, with readout performed using multiple color channels (e.g., 2 color channels, 3 color channels, 4 color channels, 5 color channels, 6 color channels, 7 color channels, 8 color channels, etc.), with suitable signal-to-noise (SNR) characteristics in relation to background fluorescence.

For multiplexed analyses, methods described involve detection of signals from a large number of partitions, where detected signals correspond to a set of color combinatorics paired with targets of a set of targets potentially represented in the sample and contained within partitions of the set of partitions, and wherein the set of targets has a total number greater than the number of color channels used to detect colors corresponding to the set of color combinatorics. In examples, the set of color combinatorics involves combinations of up to 3 colors, up to 4 colors, up to 5 colors, up to 6 colors, up to 7 colors, or greater, where each combination of colors has a corresponding target associated with the respective combination.

In one embodiment, the set of partitions involves droplets of an emulsion within a closed container, and the set of color combinatorics involves combinations of up to 3 colors, up to 4 colors, up to 5 colors, up to 6 colors, up to 7 colors, etc. detectable from each of the set of partitions. Additionally or alternatively, multiplexing involving stimulus-responsive materials can expand the number of targets that can be differentially tagged and detected by a factor equal to the number of states through which probes used to tag targets can transition. Additionally or alternatively, multiplexing involving materials that exhibit Foerster resonance energy transfer (FRET) behavior can expand the number of targets that can be differentially tagged and detected by a factor equal to the number of FRET capable probes used.

In the context of emulsion digital PCR with the numbers of partitions described, such multiplexed assay design aspects described can produce significantly improved signal-to-noise (SNR) values with reduced background, in relation to detection techniques described below (e.g., based on light-sheet imaging, etc.). In examples, the ratio of target signals (e.g., median target signals) to noise (e.g., median background noise from other partitions and/or planes of partitions) can be greater than $10^2$, greater than $10^3$, greater than $10^4$, greater than $10^5$, greater than $10^6$, greater than $10^7$, greater than $10^8$, greater than $10^9$, greater than $10^{10}$, or any intermediate value. Background noise can be attributed to fluorescence from adjacent partitions and adjacent planes of the set of planes of partitions in the context of emulsion digital PCR, or attributed to other sources with closely-positioned partitions. In examples, upon processing a sample with the processing materials, noise (e.g., median noise from other partitions and/or from other planes of partitions) can be reduced in relation to target signals by a factor of at least $10^{-2}$, $10^{-3}$, $10^{-4}$, $10^{-5}$, $10^{-6}$, $10^{-7}$, $10^{-8}$, $10^{-9}$, $10^{-10}$, or any intermediate value.

In variations, processing materials of the systems, methods, and compositions of the present disclosure described can include: a primer set comprising a common primer and a target-specific primer (or set of target-specific primers) structured to interact with the target region, the target-specific primer having a common adapter sequence, a fluorophore-labeled oligonucleotide corresponding to the common adapter sequence, the fluorophore-labeled oligonucleotide comprising a fluorophore configured to transmit a target signal if the target region is amplified, and a probe additive reagent structured to reduce background noise (e.g., from adjacent partitions and planes of partitions within the container, as described). The common primer can be a forward primer or a reverse primer. The target-specific primer can be a forward primer or a reverse primer. In specific examples, processing materials can include Taqman® probes (e.g., dual-labeled hydrolysis probes). In specific examples, processing materials can include molecular beacons or similar probe structures (e.g., probes with hairpin structures), where such probes are quenched by quenchers at regions opposite respective fluorophores when the probe is not bound to a target or in an extended configuration.

The present disclosure covers systems, devices, methods performed by such systems and devices, and compositions supporting such methods, for breaking requirements around NIPT in a high-performance and efficient manner, and with less complex instrumentation.

The systems, methods, and devices disclosed herein can provide several additional benefits over other systems and methods, and such systems, methods, and devices are further implemented into many practical applications across various disciplines.

The systems, methods, and devices disclosed herein can execute highly multiplexed molecular diagnostic assays for NIPT, other prenatal tests, and other sample characterization techniques. In specific examples, aspects of the disclosure can be used to detect various trisomies, monosomies and/or other aneuploidies in a multiplexed manner. In examples, the compositions, methods, and systems can involve testing for aneuploidies in chromosome 13, chromosome 18, and/or chromosome 21. In other examples, the compositions, methods, and systems can involving testing or characterization of aneuploidies or other genetic disorders in other chromosomes (e.g., either a whole chromosome, a partial chromosome, haplotypes, with applications down the scale to a single base location on chromosome, etc.). In specific examples, aspects of the present disclosure can be used to target genomic diseases, associated with but not limited to one or more loci associated with: chromosome 21, chromosome 18, chromosome 13, chromosome X, chromosome Y, 22q11.2 deletion/DiGeorge's Syndrome, Down syndrome, Klinefelter syndrome, XYY syndrome, XXX syndrome, Turner syndrome, partial aneuploidies, microdeletion syndromes, other chromosomal abnormalities, rare mutation detection, autosomal recessive diseases, autosomal dominant diseases, X-linked diseases, minimal residual disease, and/or other diseases. Additionally or alternatively, aspects of the present disclosure can be used for non-invasive fetal genotype determination or other applications that do not, by nature, involve diseases.

The systems, methods, and devices disclosed herein can generate chromosomal counts and differential chromosomal count ratios across different fetal fraction scenarios. In particular, due to the relatively low fetal fraction in maternal cell free DNA, a higher order level of DNA counting is required for accurate determination and in order to achieve suitable statistical confidence to distinguish between non-aneuploid and aneuploid fetuses. Current approaches for NIPT rely on platforms such as next generation sequencing (NGS) and microarrays, which are expensive with complex multi-day workflows, limiting its deployment in typical hospital laboratories. On the other hand, platforms such as digital PCR, while being a gold standard analytical platform, is at least an order of magnitude away in relation to generating levels of count suitable for diagnosis. Furthermore, other digital PCR platforms suffer from low precision due low partitioning capabilities, and rely upon Poisson correction factors. Aspects of the present disclosure include digital assay technologies that far exceed the precision of standard digital PCR platforms, and can perform at a DNA counting range akin to NGS, which makes aspects of the present disclosure suitable for NIPT. Example results thus include production of high counts (e.g., from a 10 mL sample, from a smaller than 10 mL sample, from a larger than 10 mL sample) required for NIPT fetal aneuploidy screening.

In examples, the systems, methods, and compositions described can be used to enable counting of greater than n counts, with partitioning performed in a manner such that the occupancy per template remains in the single molecule regime. Thus, there is minimal or no overlap between different template molecules with individual partitions and no statistical correction is needed (e.g., due to non-existent partitioning error). This allows the systems, methods, and compositions to enable measurement performance down to at least a 2% difference in counts (e.g., where a 2% difference in counts is equivalent to a 4% fetal fraction from fetus with trisomy or monosomy). In examples, n 50,000 counts per chromosome for each of a set of chromosomes of interest, 60,000 counts per chromosome for each of a set of chromosomes of interest, 70,000 counts per chromosome for each of a set of chromosomes of interest, 80,000 counts per chromosome for each of a set of chromosomes of interest, 90,000 counts per chromosome for each of a set of chromosomes of interest, 100,000 counts per chromosome for each of a set of chromosomes of interest, 120,000 counts per chromosome for each of a set of chromosomes of interest, 130,000 counts per chromosome for each of a set of chromosomes of interest, 140,000 counts per chromosome for each of a set of chromosomes of interest, 150,000 counts per chromosome for each of a set of chromosomes of interest, 160,000 counts per chromosome for each of a set of chromosomes of interest, 170,000 counts per chromosome for each of a set of chromosomes of interest, 180,000 counts per chromosome for each of a set of chromosomes of interest, 190,000 counts per chromosome for each of a set of chromosomes of interest, 200,000 counts per chromosome for each of a set of chromosomes of interest, 210,000 counts per chromosome for each of a set of chromosomes of interest, 220,000 counts per chromosome for each of a set of chromosomes of interest, 230,000 counts per chromosome for each of a set of chromosomes of interest, 240,000 counts per chromosome for each of a set of chromosomes of interest, 250,000 counts per chromosome for each of a set of chromosomes of interest, 260,000 counts per chromosome for each of a set of chromosomes of interest, 270,000 counts per chromosome for each of a set of chromosomes of interest, 280,000 counts per chromosome for each of a set of chromosomes of interest, 290,000 counts per chromosome for each of a set of chromosomes of interest, 300,000 counts per chromosome for each of a set of chromosomes of interest, or even other counts per chromosome for each of a set of chromosomes of interest.

In examples, the systems, methods, and compositions described can be used to generate, from a partitioned sample, greater than 50,000 counts per chromosome for each of a set of chromosomes of interest, greater than 60,000 counts per chromosome for each of a set of chromosomes of interest, greater than 70,000 counts per chromosome for each of a set of chromosomes of interest, greater than 80,000 counts per chromosome for each of a set of chromosomes of interest, greater than 90,000 counts per chromosome for each of a set of chromosomes of interest, greater than 100,000 counts per chromosome for each of a set of chromosomes of interest, greater than 120,000 counts per chromosome for each of a set of chromosomes of interest, greater than 130,000 counts per chromosome for each of a set of chromosomes of interest, greater than 140,000 counts per chromosome for each of a set of chromosomes of interest, greater than 150,000 counts per chromosome for each of a set of chromosomes of interest, greater than 160,000 counts per chromosome for each of a set of chromosomes of interest, greater than 170,000 counts per chromosome for each of a set of chromosomes of interest, greater than 180,000 counts per chromosome for each of a set of chromosomes of interest, greater than 190,000 counts per chromosome for each of a set of chromosomes of interest, greater than 200,000 counts per chromosome for each of a set of chromosomes of interest, greater than 210,000 counts per chromosome for each of a set of chromosomes of interest, greater than 220,000 counts per chromosome for each of a set of chromosomes of interest, greater than 230,000 counts per chromosome for each of a set of chromosomes of interest, greater than 240,000 counts per chromosome for each of a set of chromosomes of interest, greater than 250,000 counts per chromosome for each of a set of chromosomes of interest, greater than 260,000 counts per chromosome for each of a set of chromosomes of interest, greater than 270,000 counts per chromosome for each of a set of chromosomes of interest, greater than 280,000 counts per chromosome for each of a set of chromosomes of interest, greater than 290,000 counts per chromosome for each of a set of chromosomes of interest, greater than 300,000 counts per chromosome for each of a set of chromosomes of interest, or even greater counts per chromosome for each of a set of chromosomes of interest.

In the context of NIPT assays, maternal samples processed using compositions, according to the methods, and/or by systems described can have a fetal fraction (FF) less than 15%, less than 14%, less than 13%, less than 12%, less than 11%, less than 10%, less than 9%, less than 8%, less than 7%, less than 6%, less than 5%, less than 4%, less than 3%, or less than 2%. Percentages described are for samples without enrichment of a maternal sample by spiked-in fetal genetic material.

The systems, methods, and devices disclosed herein also include or implement multiplexed primers structured to amplify regions containing chromosome-specific probes that encode for different chromosomes (e.g., using Taqman™ assay materials with region-specific probes, using other chemistry/probes at higher plexy values, etc.). Multiplexed primer compositions can be configured for 20-plex amplification of loci of interest for each chromosome of a set of chromosomes being analyzed, 30-plex amplification of loci of interest for each chromosome of a set of chromosomes being analyzed, 40-plex amplification of loci of interest for each chromosome of a set of chromosomes being analyzed, 50-plex amplification of loci of interest for each chromosome of a set of chromosomes being analyzed, 60-plex amplification of loci of interest for each chromosome of a set of chromosomes being analyzed, 70-plex amplification of loci of interest for each chromosome of a set of chromosomes being analyzed, 80-plex amplification of loci of interest for each chromosome of a set of chromosomes being analyzed, 90-plex amplification of loci of interest for each chromosome of a set of chromosomes being analyzed, 100-plex amplification of loci of interest for each chromosome of a set of chromosomes being analyzed, or greater.

In particular, successful multiplexing at this level is attributed to the high degree of partitioning (with achievable numbers of generated partitions described) and extremely low occupancy (with achievable percent occupancies described), such that multiple molecules from the target molecules of interest (e.g., greater than 200 targets) have a minimal (or zero) probability of occupying the same partition as another target molecule. In such a high-partition and low-occupancy regime, there is no competition associated with multiple target molecules per partition, and the platform is not subject to problems related to differences in PCR efficiency between different target molecules.

As such, the disclosure provides compositions, systems, and methods for digital assays (e.g., NIPT digital assays) that are at least 90-plex, 100-plex, 110-plex, 120-plex, 130-plex, 140-plex, 150-plex, 160-plex, 170-plex, 180-plex, 190-plex, 200-plex, 210-plex, 220-plex, 230-plex, 240-plex, 250-plex, 260-plex, 270-plex, 280-plex, 290-plex, 300-plex, or greater. The set of chromosomes being analyzed can include 2 chromosomes, 3 chromosomes, 4 chromosomes, 5 chromosomes, 6 chromosomes, 7 chromosomes, 8 chromosomes, 9 chromosomes, 10 chromosomes, or greater.

Oligonucleotide compositions can be configured for multiplexed assays (e.g., locked nucleic acid (LNA) assays, Taqman assays, etc.). Such improved oligonucleotides improve sample processing, with respect to primer cleanup/removal, reduction of background, implementation of compatible forward and reverse primers for direct multiplexed assays (e.g., PCR), implementation of checks for complementarity of amplicons to non-self probes (i.e., in both sense and antisense strands), implementation of checks for complementarity of primers to probes (i.e., in both sense and antisense strands), generation of positive and negative controls for a clinical workflow, establishment of limits of detection (LoDs) and other metrics for NIPT digital assays, and/or other improvements.

The systems, methods, and devices disclosed herein can also provide a cost-effective and high resolution end-point droplet digital PCR platform that allows for DNA counting of millions of DNA targets, in a manner that can be performed with and without complex workflows such as NGS. Furthermore, aspects of the present disclosure covered in the disclosure produce a paradigm shift by encouraging widespread implementation of NIPT in decentralized laboratories around the world, by providing mechanisms for low-cost, high resolution NIPT. Aspects of the present disclosure thus have the ability to democratize NIPT by introducing a simple, yet high resolution, platform to allow NIPT and other testing to be performed in local laboratories at significantly lower cost (e.g., ~100 times lower cost). By doing this, expectant parents and healthcare providers can receive accurate NIPT results more efficiently and at significantly reduced cost, leading to better test accessibility and avoiding delay of medical decisions.

The systems, methods, and devices disclosed herein can also provide or implement non-naturally occurring compositions for facilitating assessment of biological material, amplification of nucleic acid material from isolated biological materials, constructing sequencing libraries, and sequencing nucleic acid material for characterization of said biological material. In particular, the systems, methods, and compositions are useful in achieving digital DNA counting at a scale akin to NGS in a single day workflow, and without NGS-like investments in time, instrumentation, and costs. The systems and methods described involve ultra-partitioning using centrifugation to generate partitions at an unprecedented rate, followed by counting DNA-positive droplets after amplification.

The systems, methods, and devices disclosed herein can also achieve performance of NIPT digital assay within a duration of 6 hours, within a duration of 5 hours, within a duration of 4.5 hours, within a duration of 4 hours, within a duration of 3.5 hours, within a duration of 3 hours, within a duration of 2.5 hours, within a duration of 2 hours etc. (e.g., in relation to sample partitioning, reaction time, readout, analysis, etc.).

The systems, methods, and devices disclosed herein can rapidly generate partitions (e.g., droplets from a sample fluid, droplets of an emulsion) and distributing nucleic acid material (e.g., for NIPT) across partitions, where, the device includes: a first substrate defining a reservoir comprising a reservoir inlet and a reservoir outlet; a membrane coupled to the reservoir outlet and comprising a distribution of holes; and a supporting body comprising an opening configured to retain a collecting container in alignment with the reservoir outlet. During operation, the first substrate can be coupled with the supporting body and enclose the collecting container, with the reservoir outlet aligned with and/or seated within the collecting container. During operation, the reservoir can contain a sample fluid (e.g., a mixture of nucleic acids of the sample and materials for an amplification reaction), where application of a force to the device or sample fluid generates a plurality of droplets within the collecting container at an extremely high rate (e.g., of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, of at least 4 million droplets/minute, of at least 5 million droplets/minute, of at least 6 million droplets per minute, etc.), where the droplets are stabilized in position (e.g., in a close-packed format, in equilibrium stationary positions) within the collecting container.

The systems, methods, and devices disclosed herein can rapidly generate partitions (e.g., droplets from a sample fluid, droplets of an emulsion) within a collecting container at an extremely high rate, each of the plurality of droplets including an aqueous mixture for a digital analysis, wherein upon generation, the plurality of droplets is stabilized in position (e.g., in a close-packed format, at equilibrium stationary positions, etc.) within a continuous phase (e.g., as an emulsion having a bulk morphology defined by the collecting container). In aspects, partition generation can be executed by driving the sample fluid through a distribution of holes of a membrane, where the applied force can be one or more of centrifugal (e.g., under centrifugal force), associated with applied pressure, magnetic, or otherwise physically applied.

In relation to a single-tube workflow in which the collecting container remains closed (e.g., the collecting container has no outlet, there is no flow out of the collecting container, to avoid sample contamination), method(s) can further include transmitting heat to and from the plurality of droplets within the closed collecting container according to an assay protocol. In relation to generation of emulsions having suitable clarity (e.g., with or without refractive index matching), method(s) can further include transmission of signals from individual droplets from within the closed collecting container, for readout (e.g., by an optical detection platform, by another suitable detection platform).

Where method(s) include transmitting heat to and from the plurality of droplets, within the closed container, the droplets are stable across a wide range of temperatures (e.g., 1° C. through 95° C., greater than 95° C., less than 1° C.) relevant to various digital analyses and other bioassays, where the droplets remain consistent in morphology and remain unmerged with adjacent droplets.

Examples of partition generation methods can include generating an extremely high number of droplets (e.g., greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-30 micrometers, etc.) that is relevant for digital analyses, target detection, individual molecule partitioning, or other applications.

In relation to ultra-partitioning, the disclosure provides methods for partitioning in a manner that satisfies minimum DNA counting requirements for NIPT, with a 5-logarithm dynamic range, with a 6-logarithm dynamic range, or with a higher dynamic range.

In examples, the approach discussed is designed around a simple workflow to enable deployment to local and decentralized laboratories. First, samples are carried end-to-end in the same PCR tube for user convenience and to minimize sample contamination. Second, ultra-partitioning and PCR amplification can be performed in standard laboratory equipment such as a swing bucket centrifuge and thermal cycler, lowering the infrastructure cost for ultra-high partitioning digital assay adoption. However, compositions of the disclosure can also be utilized in coordination with various technologies for isolating material in single-molecule format (e.g., by use of wells, by use of droplets, by use of other partitioning elements, etc.).

The systems, methods, and devices disclosed herein can provide efficient capture and labeling of target material (e.g., DNA, RNA, miRNA, proteins, small molecules, single analytes, multianalytes, etc.) in order to enable genomic, proteomic, and/or other multi-omic characterization of materials for various applications.

The systems, methods, and devices disclosed herein can provide a non-transitory computer readable medium comprising machine executable code that, upon execution by one or more computer processors, implements any of the methods above or elsewhere herein.

The systems, methods, and devices disclosed herein can also provide a system comprising one or more computer processors and computer memory coupled thereto. The computer memory comprises machine executable code that, upon execution by the one or more computer processors, implements any of the methods above or elsewhere herein.

Additionally or alternatively, aspects of the present disclosure can confer any other suitable benefit.

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

2. Methods and Materials

As shown in FIG. 1A, embodiments of a method 100 can include performing a non-invasive prenatal testing (NIPT) digital assay upon generating a number of counts per chromosome for a set of chromosomes present in a sample. Performing the NIPT digital assay can include: simultaneously distributing a) nucleic acids of the sample, where the nucleic acids include target loci of the set of chromosomes, and b) materials for an amplification reaction across a plurality of partitions S110; amplifying the nucleic acids with said materials for the amplification reaction, within the plurality of partitions S120; and generating the number of counts per chromosome upon detecting signals from the plurality of partitions S130. The method 100 functions to generate chromosomal counts and differential chromosomal count ratios across different fetal fraction scenarios. In particular, due to the relatively low fetal fraction in maternal cell free DNA, a higher order level of DNA counting is required for accurate determination and in order to achieve suitable statistical confidence to distinguish between non-aneuploid and aneuploid fetuses. The methods disclosed far exceed the precision of standard digital PCR platforms due to the large number of partitions involved, and can perform at a DNA counting range akin to NGS, such that the methods described are suitable for NIPT. Example results include production of high counts required for NIPT fetal aneuploidy screening.

Generating a number of counts can thus include generating an extremely large number of counts per chromosome, upon analyzing a high number of digital partitions. As such, embodiments, variations, and examples of the method 100 enable counting of greater than n counts, with partitioning performed in a manner such that that the occupancy per template remains in the single molecule regime. Thus, there is minimal or no overlap between different template molecules with individual partitions and no statistical correction is needed (e.g., due to non-existent partitioning error). In examples, upon partitioning with a high degree of partitioning at low occupancy, the number n of counts can be greater than 50,000 counts per chromosome for each of a set of chromosomes of interest, greater than 60,000 counts per chromosome for each of a set of chromosomes of interest, greater than 70,000 counts per chromosome for each of a set of chromosomes of interest, greater than 80,000 counts per chromosome for each of a set of chromosomes of interest, greater than 90,000 counts per chromosome for each of a set of chromosomes of interest, greater than 100,000 counts per chromosome for each of a set of chromosomes of interest, greater than 120,000 counts per chromosome for each of a set of chromosomes of interest, greater than 130,000 counts per chromosome for each of a set of chromosomes of interest, greater than 140,000 counts per chromosome for each of a set of chromosomes of interest, greater than 150,000 counts per chromosome for each of a set of chromosomes of interest, greater than 160,000 counts per chromosome for each of a set of chromosomes of interest, greater than 170,000 counts per chromosome for each of a set of chromosomes of interest, greater than 180,000 counts per chromosome for each of a set of chromosomes of interest, greater than 190,000 counts per chromosome for each of a set of chromosomes of interest, greater than 200,000 counts per chromosome for each of a set of chromosomes of interest, greater than 210,000 counts per chromosome for each of a set of chromosomes of interest, greater than 220,000 counts per chromosome for each of a set of chromosomes of interest, greater than 230,000 counts per chromosome for each of a set of chromosomes of interest, greater than 240,000 counts per chromosome for each of a set of chromosomes of interest, greater than 250,000 counts per chromosome for each of a set of chromosomes of interest, greater than 260,000 counts per chromosome for each of a set of chromosomes of interest, greater than 270,000 counts per chromosome for each of a set of chromosomes of interest, greater than 280,000 counts per chromosome for each of a set of chromosomes of interest, greater than 290,000 counts per chromosome for each of a set of chromosomes of interest, greater than 300,000 counts per chromosome for each of a set of chromosomes of interest, or even greater counts per chromosome for each of a set of chromosomes of interest. Method steps are described in further detail below:

2.1 Method-Sample Partitioning

Step S110 recites: simultaneously distributing a) nucleic acids of the sample, where the nucleic acids include target loci of the set of chromosomes, and b) materials for an amplification reaction across a plurality of partitions.

2.1.1 Sample and Target Aspects

In relation to sample composition, step S110 can be used to process sample types including biological fluids including or derived from blood (e.g., whole blood, peripheral blood, non-peripheral blood, blood lysate, plasma, serum, etc.), other biological fluids (e.g., urine), or other material (e.g., chorionic villus,) for NIPT. Samples can be derived from human organisms, other multicellular animals, and/or other material. In specific examples, samples processed can include maternal samples (e.g., blood, plasma, serum, urine, chorionic villus, etc.) including maternal and fetal genetic material (e.g., cellular material, cell-free nucleic acid material, other nucleic acid material, etc.) from which prenatal detection or diagnosis of genetic disorders (e.g., aneuploidies, genetically inherited diseases, other chromosomal issues, etc.) can be performed.

In the context of NIPT assays, maternal samples processed using compositions, according to the methods, and/or by systems described can have a fetal fraction (FF) less than 15%, less than 14%, less than 13%, less than 12%, less than 11%, less than 10%, less than 9%, less than 8%, less than 7%, less than 6%, less than 5%, less than 4%, less than 3%, or less than 2%. Percentages described are for samples without enrichment of a maternal sample by spiked-in fetal genetic material. In particular, for a 6% FF cutoff, the NIPT test would require at least 200,000 counts to achieve a theoretical 99.994% confidence; for a 4% FF cutoff, the NIPT test would require at least 400,000 counts to achieve a theoretical 99.994% confidence; for a 2% FF cutoff, the NIPT test would require at least 600,000 counts to achieve a theoretical 99.994% confidence, and the methods described can achieve such confidence.

In embodiments, sample targets of interest can include: nucleic acids (e.g., DNA, RNA, miRNA, etc.), where genetic targets can include one or more of: single nucleotide polymorphisms (SNPs), copy number variations (CNVs), insertions, deletions, and/or other loci of interest.

In variations, SNPs of the sample being processed and tagged in a parallel manner with materials for the amplification reaction can include SNPs can be associated with chromosomes 13, 18, 21, X, Y, and/or other chromosomes, at various loci (e.g., from 10 to 20,000 polymorphic loci); however, SNPs evaluated can additionally or alternatively be associated with other chromosomes and/or loci. Furthermore, the size of the panel of targets can be determined based upon the likelihood of detecting at least one SNP that is homozygous in the mother and heterozygous in the fetus. SNPs associated with any chromosome can have a minor allele fraction (MAF) greater than 0.4. SNPs evaluated can alternatively be characterized by MAF above another suitable threshold (e.g., MAF>0.2, MAF>0.3, etc.). SNPs evaluated can be for coding regions (e.g., synonymous, non-synonymous, missense, nonsense) and/or non-coding regions. SNPs evaluated can be biallelic or multiallelic, with more than two alleles per SNP.

The size of the SNP panel being evaluated, threshold MAF for each SNP, and chromosomal distribution can thus be selected to optimize or otherwise increase the probability of returning NIPT characterizations, based upon the methods described.

Furthermore, SNPs selected for evaluation can have allele pairs that are well-discriminated (e.g., with respect to stabilizing-destabilizing characteristics). For instance, SNPs can be selected with prioritization of G/T, C/A, and T/A SNPs having high destabilization strength characteristics.

2.1.2 Partitioning Aspects

Examples of partition generation techniques in relation to Step S110 can include generating, from the sample combined with materials for reactions, an extremely high number of droplets (e.g., greater than 5 million droplets, greater than 6 million droplets, greater than 7 million droplets, greater than 8 million droplets, greater than 9 million droplets, greater than 10 million droplets, greater than 15 million droplets, greater than 20 million droplets, greater than 25 million droplets, greater than 30 million droplets, greater than 40 million droplets, greater than 50 million droplets, greater than 100 million droplets, etc.) within a collecting container having a volumetric capacity (e.g., less than 50 microliters, from 50 through 100 microliters and greater, etc.), where droplets have a characteristic dimension (e.g., from 1-50 micrometers, from 10-30 micrometers, etc.) that is relevant for digital analyses, target detection, individual molecule partitioning, or other applications.

As described above, partitioning is conducted in a manner such that each partition has one or zero molecules, such that the partitions are characterized as having low occupancy (e.g., less than 15% occupancy of partitions by individual molecules, less than 14% occupancy of partitions by individual molecules, less than 13% occupancy of partitions by individual molecules, less than 12% occupancy of partitions by individual molecules, less than 11% occupancy of partitions by individual molecules, less than 10% occupancy of partitions by individual molecules, less than 9% occupancy of partitions by individual molecules, less than 8% occupancy of partitions by individual molecules, less than 7% occupancy of partitions by individual molecules, less than 6% occupancy of partitions by individual molecules, less than 5% occupancy of partitions by individual molecules, less than 4% occupancy of partitions by individual molecules, etc.).

Figure 1B:
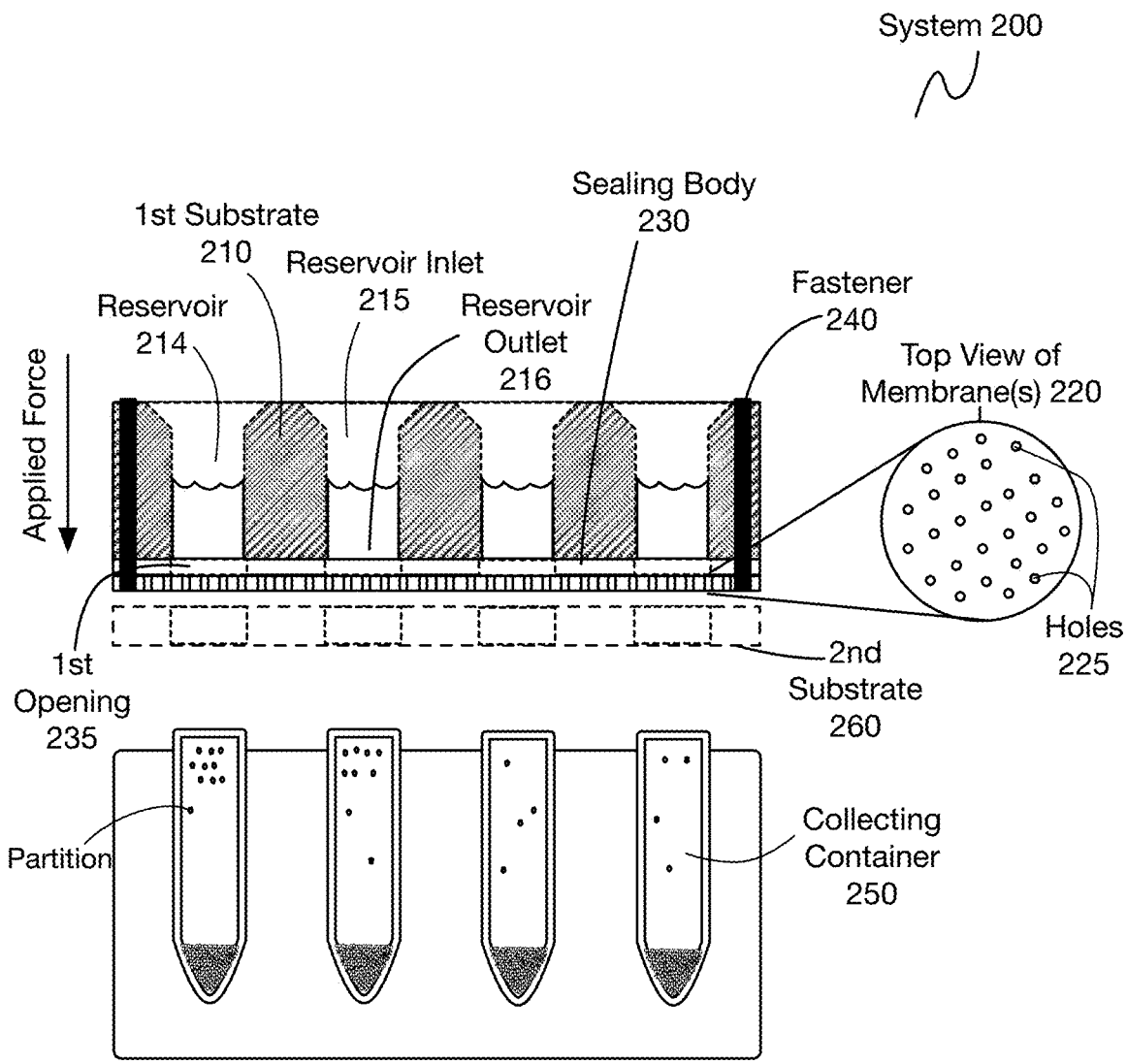
FIG. 1B depicts a schematic of an embodiment of a system involved in performance of a digital NIPT assay.

Embodiments, variations, and examples of the methods described can be implemented by or by way of embodiments, variations, and examples of components of system 200 shown in FIG. 1B, with a first substrate 210 defining a set of reservoirs 214 (for carrying sample/mixtures for droplet generation), each having a reservoir inlet 215 and a reservoir outlet 216; one or more membranes (or alternatively, droplet-generating substrates) 220 positioned adjacent to reservoir outlets of the set of reservoirs 214, each of the one or more membranes 220 including a distribution of holes 225; and optionally, a sealing body 230 positioned adjacent to the one or more membranes 120 and including a set of openings 235 aligned with the set of reservoirs 214; and optionally, one or more fasteners (including fastener 240) configured to retain the first substrate 210, the one or more membranes 220, and optional sealing body 230 in position relative to a set of collecting containers 250. In variations, the system 100 can additionally include a second substrate 260, wherein the one or more membranes 220 and optionally, the sealing body 230, are retained in position between the first substrate 210 and the second substrate 260 by the one or more fasteners. In using embodiments, variations, and examples of the system 200, material derived from each sample is retained in its own tube and does not require batching and pooling, allowing for scalable batch size.

In variations, the distribution of holes 225 can be generated in bulk material with specified hole diameter(s), hole depth(s) (e.g., in relation to membrane thickness), aspect ratio(s), hole density, and hole orientation, where, in combination with fluid parameters, the structure of the membrane can achieve desired flow rate characteristics, with reduced or eliminated polydispersity and merging, suitable stresses (e.g., shear stresses) that do not compromise the single cells but allow for partitioning of the single cells, and steady formation of droplets (e.g., without jetting of fluid from holes of the membrane).

In variations, the hole diameter can range from 0.2 micrometers to 30 micrometers, and in examples, the holes can have an average hole diameter can be 0.02 micrometers, 0.04 micrometers, 0.06 micrometers, 0.08 micrometers, 0.1 micrometers, 0.5 micrometers, 1 micrometers, 2 micrometers, 3 micrometers, 4 micrometers, 5 micrometers, 6 micrometers, 7 micrometers, 8 micrometers, 9 micrometers, 10 micrometers, 20 micrometers, 30 micrometers, any intermediate value, or greater than 30 micrometers (e.g., with use of membrane having a thickness greater than or otherwise contributing to a hole depth greater than 100 micrometers).

In variations, the hole depth can range from 1 micrometer to 200 micrometers (e.g., in relation to thickness of the membrane layer) or greater, and in examples the hole depth (e.g., as governed by membrane thickness) can be 1 micrometers, 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or any intermediate value.

In variations, the hole aspect ratio can range from 5:1 to 200:1, and in examples, the hole aspect ratio can be 5:1, 10:1, 20:1, 30:1, 40:1, 50:1, 60:1, 70:1, 80:1, 90:1, 100:1, 125:1, 150:1, 175:1, 200:1, or any intermediate value.

In variations, the hole-to-hole spacing can range from 5 micrometers to 200 micrometers or greater, and in examples, the hole-to-hole spacing is 5 micrometers, 10 micrometers, 20 micrometers, 30 micrometers, 40 micrometers, 50 micrometers, 60 micrometers, 70 micrometers, 80 micrometers, 90 micrometers, 100 micrometers, 125 micrometers, 150 micrometers, 175 micrometers, 200 micrometers, or greater. In a specific example, the hole-to-hole spacing is greater than 10 micrometers.

In examples, the hole orientation can be substantially vertical (e.g., during use in relation to a predominant gravitational force), otherwise aligned with a direction of applied force through the distribution of holes, or at another suitable angle relative to a reference plane of the membrane or other droplet generating substrate 120.

Additionally or alternatively, embodiments, variations, and examples of the methods described can be implemented by or by way of embodiments, variations, and examples of components described in U.S. application Ser. No. 17/687, 080 filed 4 Mar. 2022 and U.S. Pat. No. 11,242,558 granted 8 Feb. 2022, each of which is herein incorporated in its entirety by this reference.

Step S110 can further include generating droplets at an extremely high rate. In examples, the rate can be a rate of at least 200,000 droplets/minute, of at least 300,000 droplets/minute, of at least 400, droplets/minute, of at least 500,000 droplets/minute, of at least 600,000 droplets/minute, of at least 700,000 droplets/minute, of at least 800,000 droplets/minute, of at least 900,000 droplets/minute, of at least 1 million droplets/minute, of at least 2 million droplets/minute, of at least 3 million droplets/minute, of at least 4 million droplets/minute, of at least 5 million droplets/minute, of at least 6 million droplets per minute, or greater, using embodiments, variations, and examples of system elements described above. Droplets can be generated at the high rate, using embodiments, variations, and examples of the membrane(s) described above, in relation to hole density, hole-to-hole spacing, hole diameter, membrane thickness, hole aspect ratio, membrane material, and/or other characteristics.

In relation to droplet generation in Step S110, an extremely high number of droplets can be generated within a collecting container, wherein, in variations, greater than 2 million droplets, greater than 3 million droplets, greater than 4 million droplets, greater than 5 million droplets, greater than 6 million droplets, greater than 7 million droplets, greater than 8 million droplets, greater than 9 million droplets, greater than 10 million droplets, greater than greater than 15 million droplets, greater than 20 million droplets, greater than 25 million droplets, greater than 30 million droplets, greater than 40 million droplets, greater than 50 million droplets, greater than 100 million droplets, greater than 200 million droplets, greater than 300 million droplets, or greater can be generated within the collecting container.

Generating the plurality of droplets in Step S110 can include driving the sample combined with materials for the amplification reaction, through a membrane or other substrate (e.g., microchannel array plate) comprising a distribution of holes, the membrane or other substrate aligned with or coupled to a reservoir outlet of a reservoir for the sample fluid. The membrane/substrate can be coupled to a reservoir outlet of a reservoir for the sample fluid and the collecting container can be aligned with the substrate, downstream of the substrate, in order to receive the generated droplets. As such, methods described can include distributing targets and materials for tagging and amplifying the targets, across a plurality of droplets of an emulsion (e.g., using systems and materials as described above), upon driving a mixture comprising the set of single cells and the set of functionalized particles through a substrate having a distribution of holes. In relation to generation of the emulsion, the mixture can be driven through the holes of the substrate into one or more fluid layers, such that the droplets are stabilized within an emulsion.

Driving the sample fluid can include applying a centrifugal force (e.g., by centrifugation) to drive the sample fluid through the holes of the membrane. In variations, the centrifugal force can be applied at 1,000 g, 2,000 g, 3,000 g, 4,000 g, 5,000 g, 6,000 g, 7,000 g, 8,000 g, 9,000 g, 10,000 g, 11,000 g, 12,0000 g, 13,000 g, 14,000 g, 15,000 g, 16,000 g, 17,000 g, 18,000 g, 19,000 g, 20,000 g, 30,000 g, any intermediate value, or greater than 30,000 g. Duration of spinning can be 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 40 minutes, 50 minutes, any intermediate value, or greater than 50 minutes, where spin duration is a function of the amount of sample fluid being dropletized.

However, in alternative variations, the applied force can be associated with an applied pressure, magnetically applied, or otherwise physically applied to drive sample fluid(s) through the membrane(s) or other substrates.

In relation to components of the sample fluid and/or fluid layers within the collecting container(s) for generation of an emulsion, the sample fluid and fluid layers within the collecting container can have one or more of a certain density, viscosity, surface tension, aqueous nature, hydrophobicity, immiscibility characteristics, or other characteristics. Sample fluids and/or fluid layers can further include materials described in U.S. Pat. No. 11,162,136 granted on 2 Nov. 2021, incorporated by reference above, where, in one such embodiment, a collecting container contains an oil layer covering an aqueous layer, and the sample fluid is driven through the substrate into the collecting container to generate an emulsion of the plurality of droplets separated from each other by a continuous phase. Further, droplets and/or resulting emulsions generated with said droplets can have a high degree and greater than a threshold level of clarity, with or without refractive index matching. In variations, the threshold level of clarity of the emulsion is associated with a transmissivity greater than 50% transmissivity, greater than 60% transmissivity, greater than 70% transmissivity, greater than 80% transmissivity, greater than 90% transmissivity, greater than 95% transmissivity, greater than 99% transmissivity, etc., upon measuring clarity of the emulsion using a transmission detector.

Materials of the emulsions described can further prevent leakage of contents (e.g., mRNAs, nucleic acids, nuclear components, proteins, other analytes, etc.) from one partition to another, thereby enabling isolation of targets throughout sample processing and downstream analyses.

While methods of droplet generation are described above in relation to Step S110, partitioning can alternatively be performed by distribution of the sample combined with the set of processing materials across a set of containers (e.g., microwells, nanowells, etc.). Partitioning can still alternatively be performed by distributing the sample combined with the set of processing materials across a substrate (e.g., as spots) and/or in another suitable manner.

2.1.1 Materials for Tagging and Amplification of Sample Targets

To enable chromosomal counting according to the performance specifications described, materials for the amplification reaction distributed across partitions in Step S110 function to enable tagging and amplification of the sample targets in parallel. As such, materials for the amplification reaction can include multiplexed primer panels targeting loci of interest for each of the set of chromosomes, probes (e.g., fluorophore-conjugated probes corresponding to targets of interest for the NIPT assay) and quenchers for enabling optical detection of tagged and amplified targets using the primer panels (where optical detection for generating the number of counts is described in relation to Step S130 below), polymerase (e.g., Taq polymerase), dNTPs, and buffer components. As such, materials for the amplification reaction can include primer panels with a master mixture having a cassette (e.g., FRET cassette) including a dye/fluorophore with complementary quencher for each target or target variation, a polymerase (e.g., Taq polymerase), dNTPs, and buffer components.

Oligonucleotide compositions can be configured for multiplexed assays (e.g., locked nucleic acid (LNA) assays, Taqman assays, etc.). Such improved oligonucleotides improve sample processing, with respect to primer cleanup/removal, reduction of background, implementation of compatible forward and reverse primers for direct multiplexed assays (e.g., PCR), implementation of checks for complementarity of amplicons to non-self probes (i.e., in both sense and antisense strands), implementation of checks for complementarity of primers to probes (i.e., in both sense and antisense strands), generation of positive and negative controls for a clinical workflow, establishment of limits of detection (LoDs) and other metrics for NIPT digital assays, and/or other improvements.

In more detail, the multiplexed primer panels include primers structured to flank chromosome-specific probes that encode for different chromosomes. Multiplexed primer compositions can be configured for 30-plex amplification of loci of interest for each chromosome of a set of chromosomes being analyzed, 40-plex amplification of loci of interest for each chromosome of a set of chromosomes being analyzed, 50-plex amplification of loci of interest for each chromosome of a set of chromosomes being analyzed, 60-plex amplification of loci of interest for each chromosome of a set of chromosomes being analyzed, 70-plex amplification of loci of interest for each chromosome of a set of chromosomes being analyzed, 80-plex amplification of loci of interest for each chromosome of a set of chromosomes being analyzed, 90-plex amplification of loci of interest for each chromosome of a set of chromosomes being analyzed, 100-plex amplification of loci of interest for each chromosome of a set of chromosomes being analyzed, or greater.

As such, the disclosure provides compositions, systems, and methods for digital assays (e.g., NIPT digital assays) that are at least 90-plex, 100-plex, 110-plex, 120-plex, 130-plex, 140-plex, 150-plex, 160-plex, 170-plex, 180-plex, 190-plex, 200-plex, 210-plex, 220-plex, 230-plex, 240-plex, 250-plex, 260-plex, 270-plex, 280-plex, 290-plex, 300-plex, or greater. The set of chromosomes being analyzed can include 2 chromosomes, 3 chromosomes, 4 chromosomes, 5 chromosomes, 6 chromosomes, 7 chromosomes, 8 chromosomes, 9 chromosomes, 10 chromosomes, or greater.

Figure 2:
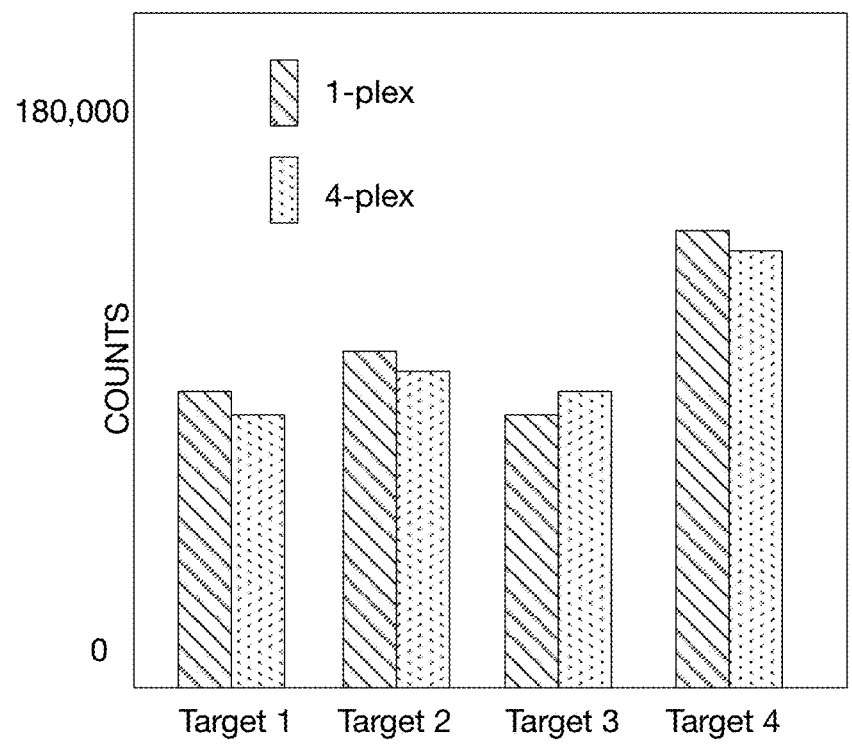
FIG. 2 depicts example multiplexing performance results for each of a set of fluorophore colors corresponding to targets.

FIG. 2 depicts example multiplexing performance for each of a set of fluorophore colors corresponding to targets.

Concentrations of primers (e.g., forward primers, reverse primers) can be approximately 50 nM in solution, 60 nM in solution, 70 nM in solution, 80 nM in solution, 90 nM in solution, 100 nM in solution, 110 nM in solution, 120 nM in solution, 130 nM in solution, 140 nM in solution, 150 nM in solution, 160 nM in solution, 170 nM in solution, 180 nM in solution, 190 nM in solution, 200 nM in solution, 300 nM in solution, 400 nM in solution, 500 nM in solution, 600 nM in solution, or alternatively less than 50 nm or greater than 600 nM in solution.

Concentrations of reporter oligonucleotides (e.g., fluorescent oligonucleotides) can be approximately 30 nM in solution, 40 nM in solution, 50 nM in solution, 60 nM in solution, 70 nM in solution, 80 nM in solution, 90 nM in solution, 100 nM in solution, 110 nM in solution, 120 nM in solution, 130 nM in solution, 140 nM in solution, 150 nM in solution, 160 nM in solution, 170 nM in solution, 180 nM in solution, 190 nM in solution, 200 nM in solution, or alternatively less than 30 nm or greater than 200 nM in solution.

Concentrations of quencher oligonucleotides can be approximately 100 nM in solution, 110 nM in solution, 120 nM in solution, 130 nM in solution, 140 nM in solution, 150 nM in solution, 160 nM in solution, 170 nM in solution, 180 nM in solution, 190 nM in solution, 200 nM in solution, 300 nM in solution, 400 nM in solution, 500 nM in solution, 600 nM in solution, or alternatively less than 100 nm or greater than 600 nM in solution.

With respect to labels implemented for the primers and corresponding dyes/fluorophore families implemented for the cassette of the master mixture, dyes/fluorophores can be associated with chemical families including: acridine derivatives, arylmethine derivatives, anthracene derivatives, tetrapyrrole derivatives, xanthene derivatives, oxazine derivatives, dipyrromethene derivatives, cyanine derivatives, squaraine derivates, squaraine rotaxane derivatives, naphthalene derivatives, coumarin derivatives, oxadiazole derivatives, pyrene derivatives, and/or other chemicals. Such fluorophores can further be attached to other functional groups as needed for tagging of targets in a detectable manner.

In examples, dyes (e.g., for tagging of RNAs, DNAs, oligonucleotides, etc.) can include one or more of: FAM, (e.g., 6-FAM), Cy3™, Cy5™, Cy5.5™, TAMRA™ (e.g., 5-TAMRA, 6-TAMRA, etc.), MAX, JOE, TET™, ROX, TYE™ (e.g., TYE 563, TYE 665, TYE 705, etc.), Yakima Yellow®, HEX, TEX (e.g., TEX 615), SUN, ATTO™ (e.g., ATTO 488, ATTO 532, ATTO 550, ATTO 565, ATTO Rho101, ATTO 590, ATTO 633, ATTO 647, etc.), Alexa Fluor® (e.g., Alexa Fluor 488, Alexa Fluor 532, Alexa Fluor 546, Alexa Fluor 594, Alexa Fluor 647, Alexa Fluor 660, Alexa Fluor 750, etc.), IRDyes® (e.g., 5'IRDye 700, 5'IRDye 800, 5'IRDye 800CW, etc.), Rhodamine (e.g., Rhodamine Green, Rhodamine Red, Texas Red®, Lightcycler®, Dy 750, Hoechst dyes, DAPI dyes, SYTOX dyes, chromomycin dyes, mithramycin dyes, YOYO dyes, ethidium bromide dyes, acridine orange dyes, TOTO dytes, thiazole dyzes, CyTRAK dyes, propidium iodide dyes, LDS dyes, and/or other dyes.

Dyes/fluorophores implemented can correspond to wavelength ranges in the visible spectrum and/or non-visible spectrum of electromagnetic radiation. Furthermore, dyes/fluorophores implemented can be configured to prevent overlapping wavelengths (e.g., of emission) and/or signal bleed through with respect to multiplexed detection. In variations, the set of processing materials can include components for up to 6 wavelength ranges for multiplexed detection of targets; however, the set of processing materials can include components for less than 6 wavelength ranges (e.g., one wavelength, two wavelengths, three wavelengths, four wavelengths, five wavelengths) or more than 6 wavelength ranges.

Furthermore, with respect to different wavelength ranges, different targets can be matched with dye/fluorophore colors in a manner that promotes discrimination of results (e.g., without overlap) upon detection of signals from processed sample material.

Quencher oligonucleotides implemented can include a quencher molecule configured such that, when the quencher oligonucleotide anneals with a primer having a fluorophore, the quencher molecule is in proximity to (e.g., directly opposite) the fluorophore in order to quench the fluorophore. Additionally or alternatively, quenchers can include one or more of: black hole quenchers, static quenchers, self-quenchers (e.g., fluorophores that self-quench under certain conditions by producing secondary structures or other structures), and/or other suitable quenchers.

Probes implemented can include Taqman™ probes and/or other dual-labeled probes to differentiate alleles of a target region. Quenchers of Taqman™ and/or other dual-label probes can be configured to quench signal of the fluorophore if the quencher is in proximity to the fluorophore below a threshold distance). Additionally or alternatively, quenchers can include one or more of: black hole quenchers, static quenchers, self-quenchers (e.g., fluorophores that self-quench under certain conditions by producing secondary structures or other structures), and/or other suitable quenchers. Quenchers can be used to suppress background signals (e.g., for 3D imaging applications, for other detection applications).

Materials for the amplification reaction can additionally or alternatively include implementation of components structured to improve signal-to-noise ratio (SNR) characteristics in the context of multiplexed detection, by increasing signal characteristics and/or reducing background (e.g., noise other artifacts). The components can include one additive for each wavelength range/color for detection (as opposed to one additive for each target/SNP being evaluated). Additionally or alternatively, the additives can have from 5-20 bases or another suitable number of bases. Additionally or alternatively, modified nucleic acids (e.g., such as locked nucleic acids (LNA) or other modified nucleic acids) can be incorporated into forward and/or reverse primers of the materials to improve SNR. In variations, LNA content can occupy a percentage (e.g., 10-60% LNA content) of the respective primer to improve SNR, where LNA content can be biased toward the 3' end, the 5' end, or intermediate the 3' and 5' ends.

However, the set of processing materials can additionally or alternatively include other suitable components and/or be configured in another suitable manner.

First Example—Primer Design: Embodiments, variations, and examples of the present disclosure also cover oligonucleotide compositions for primer panels and designs thereof for multiplexed assays (e.g., with locked nucleic acids (LNA), with Taqman™ materials, etc.). Such improved oligonucleotides improve sample processing, with respect to primer cleanup/removal, reduction of background, implementation of compatible forward and reverse primers for direct multiplexed assays (e.g., PCR), implementation of checks for complementarity of amplicons to non-self probes (i.e., in both sense and antisense strands), implementation of checks for complementarity of primers to probes (i.e., in both sense and antisense strands), generation of positive and negative controls for a clinical workflow, establishment of limits of detection (LoDs) and other metrics for NIPT digital PCR assays, and/or other improvements.

In one example for an aneuploidy assay associated with chromosome 21, chromosome 18, chromosome 13, chromosome X, and chromosome Y, variations of probes and/or wobbles (e.g., for longer chromosomes such as chromosome X) can be configured with: a desired probe sequence, a locked nucleic acid (LNA) probe (e.g., with avoidance of positioning Affinity Plus LNA bases on the first or last bases of the probe sequence, with up to 6 LNA bases, with additional Affinity Plus LNA bases incorporated to adjust Tm, etc.), a desired Tm (e.g., from 15-85C), an associated channel (e.g., for fluorescent detection), a probe additive, a number of probes, a number of probe additives, desired compatibility of LNA probes with universal primers (e.g., SP1 and SP2, U1 and U2, etc.), with minimal interactions with the LNA probes in the solution (e.g., at the 3' end of probe and 5' end of primer), otherwise probes might be cleaved via primer/probe interactions and result in high background; and other aspects.

In examples, determining candidate regions for probes can include: mapping all locations for the candidate probe on the respective chromosome (e.g., probe sequence on sense strand, and reverse complement of the probe sequence on the anti-sense strand); cross-checking candidate locations and eliminating those within known copy number variations (CNVs); eliminating candidate locations if the probe sequence occurs only once in +/−50 bp of each location of the probe (or alternatively, another threshold distance such as 30 bp, 40 bp, 60 bp, 70 bp, 80 bp, 90 bp, etc.); eliminated candidate locations, if the region +/−50 bp from the candidate probe location (or alternatively, another threshold distance such as 30 bp, 40 bp, 60 bp, 70 bp, 80 bp, 90 bp, etc.) contains complementarity to any of the probes other than those intended for its chromosome (e.g., with a criteria for elimination including: sense and antisense strand of amplicons with 8 or more perfect matches to non-self probes); eliminating candidate locations, if the region +/−50 bp of the candidate location (or alternatively, another threshold distance such as 30 bp, 40 bp, 60 bp, 70 bp, 80 bp, 90 bp, etc.) contains a common SNP; and other suitable constraints.

In examples, evaluating primers can include: evaluation of specific forward and reverse primers in a prioritized manner (e.g., with evaluation of chromosome Y forward and reverse primers); determination of no hairpin or undesired structures after addition of universal primer handles; elimination of candidate primers with significant interaction with any probes (e.g., selecting based on alignment of reverse complement of primer vs. probe; length >=10, where interactions can result in cleavage of the probe and increased background; alignment of primer (sense sequence) vs. probe, where interactions can cause probe additives to adhere to primers instead of the probes, leading to elevated background, etc.); determination of minimal primer-dimer interaction towards the 3' ends of forward and reverse primers; selection of forward and reverse primer pairs that amplify only 1 unique genome location; selecting based upon distance between candidate probe regions on each chromosome; delta G values; delta H values; delta S values; and other evaluation aspects.

In particular, in the context of emulsion digital PCR with the numbers of partitions described, such multiplexed assay design aspects described can produce significantly improved signal-to-noise (SNR) values with reduced background, in relation to detection techniques described below (e.g., based on lightsheet imaging, etc.). In examples, target signals can be at least $10^2$ greater than background noise signals, $10^3$ greater than background noise signals, $10^4$ greater than background noise signals, $10^5$ greater than background noise signals, $10^6$ greater than background noise signals, $10^7$ greater than background noise signals, or better. Background noise can be attributed to fluorescence from adjacent partitions and adjacent planes of the set of planes of partitions in the context of emulsion digital PCR, or attributed to other sources with closely-positioned partitions.

In examples associated with reaction materials described and used for droplet digital PCR, determining the target signal value can include: for each plane of a set of planes of partitions under interrogation (e.g., by lightsheet detection, by another method of detection, etc.): determining a categorization based upon a profile of positive partitions represented in a respective plane, determining a target signal distribution and a noise signal distribution specific to the profile, and determining a target signal intensity and a noise signal intensity for the respective plane. Here, the target signal value can be an average value (or other representative value) of the target signal intensities determined from the set of planes, and the background noise signal value can be an average value (or other representative value) of the noise signal intensities determined from the set of planes.

However, materials used for the amplification and/or detection reactions can be otherwise configured to improve SNR.

2.2 Sample Processing and Amplification within Partitions

Step S120 recites: amplifying the nucleic acids with the materials for the amplification reaction, within the plurality of partitions.

Upon distribution of the nucleic acids of the sample with the materials described in relation to Step S110, the amplification reaction can include: denaturation of template material (e.g., nucleic acid template material); promoting annealing of materials (e.g., with primer/probe materials of the multiplexed primer set) to target regions of interest for the NIPT assay or other assay; and amplification of the target regions of interest with thermocycling, to generate amplicons tagged with probes for detection in relation to Step S130.

Step S130 can include multiple cycles to produce a detectable signal, whereby levels of tagged target sequences increase until a detection threshold is reached and/or surpassed. For each cycle, labeled oligonucleotides can bind to new complementary sequences, releasing fluorophores from corresponding quenchers to produce detectable signals for each target (e.g., target associated with the NIPT assay, other assay) present in the sample. However, fluorophores corresponding to targets that are not present are not released and thus continue to be quenched during rounds of amplification.

In particular, with regard to parameters associated with threshold cycles at which or beyond which amplified targets become detectable (e.g., $C_t$, $C_p$, $C_q$, etc.), step S130 can further include detecting and/or returning results indicative of target presence prior to the end-point of the process and/or at the end-point of the process (e.g., as in end-point PCR). Additionally or alternatively, real-time measurement of signals can be performed contemporaneously with each cycle of amplification.

In relation to the one or more stages of sample processing, activation-associated aspects can be performed at a temperature or temperature profile (e.g., 90° C., 91° C., 92° C., 93° C., 94° C., 95° C., another suitable temperature), for a duration of time (e.g., 10 minutes, 12 minutes, 15 minutes, another suitable duration of time), and/or for a number of cycles (e.g., 1 cycle, 2 cycles, another suitable number of cycles). In relation to the amplification processes performed in Step S130, denaturation-associated aspects can be performed at a temperature (e.g., 90° C., 91° C., 92° C., 93° C., 94° C., 95° C., another suitable temperature) or temperature profile, for a duration of time (e.g., 10 seconds, 15 seconds, 20 seconds, 25 seconds, another suitable duration of time), and/or for a number of cycles (e.g., 1 cycle, 5 cycles, 10 cycles, 20 cycles, another suitable number of cycles). In relation to the amplification processes performed in Step S130, annealing/elongation-associated aspects can be performed at a temperature or temperature profile (e.g., 52-70° C. with a ramp down rate, another suitable temperature profile), for a duration of time (e.g., 20 seconds, 30 seconds, 60 seconds, 90 seconds, another suitable duration of time), and/or for a number of cycles (e.g., 1 cycle, 5 cycles, 10 cycles, 20 cycles, 25 cycles, 30 cycles, another suitable number of cycles).

FIG. 3 depicts an example multiplexed amplification process using example multiplexed primers.

However, amplification within partitions can be performed in another suitable manner.

2.3 Target Detection and Generation of Count Parameters

Step S130 recites: generating said counts per chromosome upon detecting signals from the plurality of partitions. Step S130 functions to enable detection of signals from dyes/fluorophores that are released upon processing the sample with the materials described in relation to Step S110 above, thereby providing indications of presence of targets (e.g., targets for the NIPT assay, other targets for other assays) which can be counted. In particular, with regard to parameters associated with threshold cycles at which or beyond which amplified targets become detectable (e.g., $C_t$, $C_p$, $C_q$, etc.), step S130 can include detecting and/or returning results indicative of target presence prior to the end-point of the process and/or at the end-point of the process (e.g., as in end-point PCR). Additionally or alternatively, real-time measurement of signals can be performed contemporaneously with each cycle of amplification.

In variations, detection of signals can include irradiating processed sample material with suitable excitation wavelengths of light, and/or receiving emitted wavelengths of light corresponding to released dyes/fluorophores. As such detection of signals can be implemented by an optical signal detection subsystem (e.g., imaging subsystem). In particular, detection subsystems can be structured for detection of signals from partitions (e.g., by light sheet imaging, by fluorescence microscopy, by confocal microscopy, by another suitable optical detection subsystem, etc.) using combinations of filters and/or color channels, where signals from individual partitions are detected in a high-partition number but low-occupancy regime. As such, detection can be performed for partitions arranged in 3D (e.g., as in droplets of an emulsion within a closed container, as in droplets stabilized in bulk format within a container, as in droplets stabilized in a close-packed volumetric configuration), in 2D (e.g., for a monolayer or bi-layer of partitions at a substrate), and/or in another suitable format. With respect to sample processing using the set of processing materials, reactions within individual partitions can thus produce signals that are detected by systems that can detect signals from multiple partitions or all partitions simultaneously in a distinguishable manner. Alternatively, reactions within individual partitions can produce signals that are detected by systems that can detect signals from individual partitions in a sequential manner.

Figure 4:
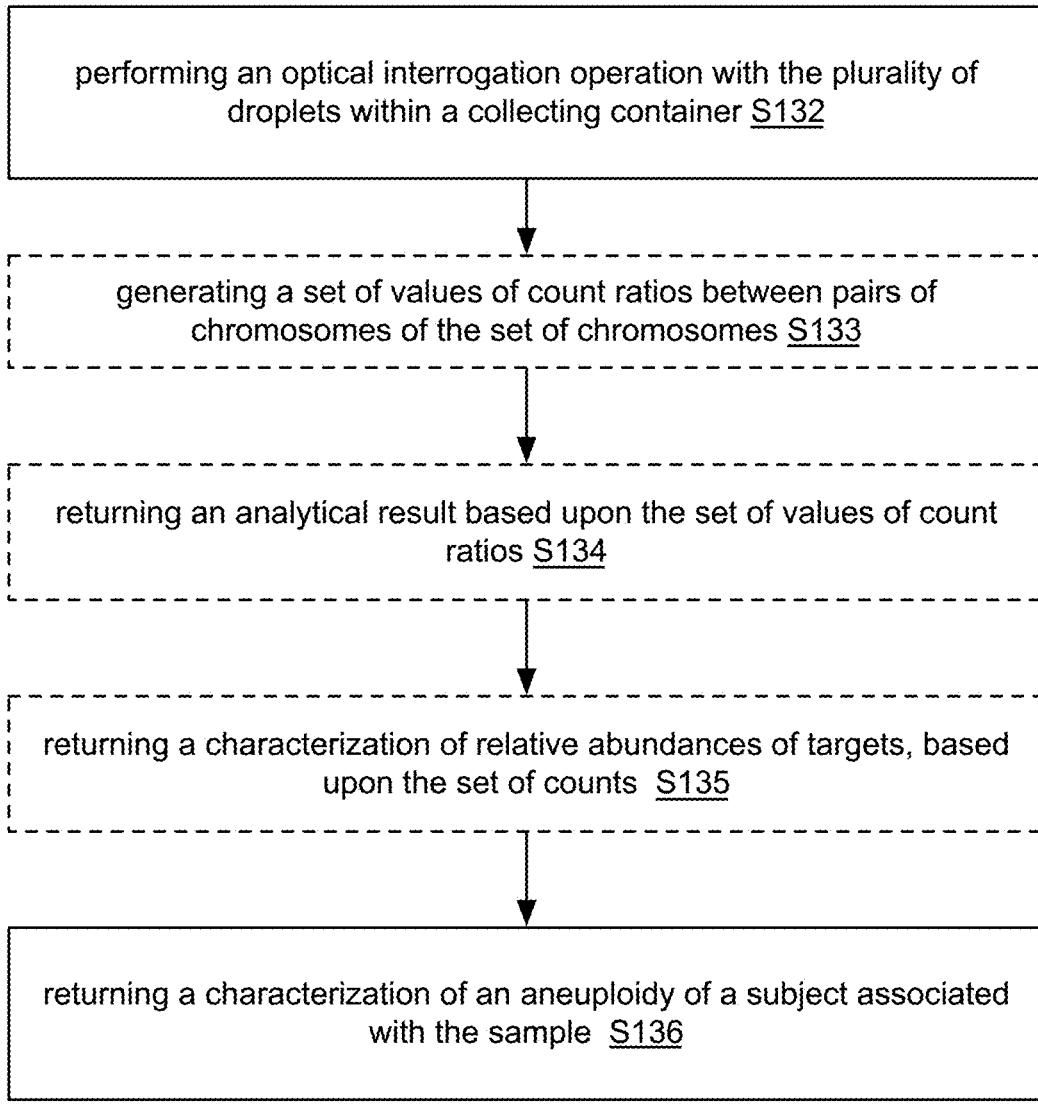
FIG. 4 depicts a flowchart of an embodiment of a portion of a method for performance of a digital assay.

In one variation, as shown in FIG. 4, the method can include: performing an optical interrogation operation with the plurality of droplets within a collecting container S132, where the optical interrogation operation can include readout of signals from droplets of the plurality of droplets. In particular, readout can be performed for cross sections of the plurality of droplets within the collecting container, using techniques described in applications incorporated by reference. Readout of fluorescent signals (e.g., from labeled analytes within droplets of the dispersed phase, from products of analytes within droplets of the dispersed phase, etc.) can be performed by one or more of a 3D scanning technique (e.g., light sheet imaging, confocal microscopy, etc.) and a planar imaging technique (e.g., to take images of a cross-section of the closed container). Additionally or alternatively, in some applications, readout of colorimetric changes associated with droplets of the dispersed phase can be performed by 3D imaging techniques (e.g., 3D brightfield construction using light field imaging, etc.).

Readout can be performed for each of a set of cross sections of the plurality of droplets/collecting container, across multiple color channels (e.g., 2 color channels, three color channels, four color channels, five color channels, six color channels, seven color channels, etc.).

Readout can be performed for 10 cross-sections of the plurality of droplets, 20 cross-sections of the plurality of droplets, 30 cross-sections of the plurality of droplets, 40 cross-sections of the plurality of droplets, 50 cross-sections of the plurality of droplets, 60 cross-sections of the plurality of droplets, 70 cross-sections of the plurality of droplets, 80 cross-sections of the plurality of droplets, 90 cross-sections of the plurality of droplets, 100 cross-sections of the plurality of droplets, 200 cross-sections of the plurality of droplets, 300 cross-sections of the plurality of droplets, 400 cross-sections of the plurality of droplets, 500 cross-sections of the plurality of droplets, 600 cross-sections of the plurality of droplets, any intermediate value, or greater, within the closed collecting container, for each of the set of color channels.

In specific examples, readout associated with digital analyses (e.g., counting, quantification, etc.) for the NIPT assay or other assay, for each channel, can be performed within a duration of 5 minutes, 4 minutes, 3 minutes, 2 minutes, 1 minute, 30 seconds, 20 seconds, 10 seconds, or less, depending upon one or more of signal-to-noise ratio, optical sensor sensitivity, excitation power (e.g., of a light source used to illuminate droplets and induce fluorescence), or other characteristics.

In other variations, readout of non-fluorescent signals from droplets of the dispersed phase can be performed. For instance, products resulting from reactions within individual droplets of the dispersed phase can produce changes in one or more of refractive indices, light absorption, light scattering, light reflection, light transmission, or other light interaction characteristics that are different from empty or unreacted droplets, for detection by various techniques (e.g., spectrophotometric techniques, turbidimetric techniques, etc.).

Readout thus involves generation of data indicating partitions from which positive signals are emitted, and corresponding fluorophores (or other discriminating features) associated with the positive signals.

After performing the optical interrogation operation, the method 100 can include transforming data representing positive signals and corresponding fluorophores (or other discriminating features) associated with the positive signals, into counts for loci of interest for each of the set of chromosomes.

Counts can be generated at the chromosome level (e.g., for chromosomes 13, 18, 21, X, and/or Y) and/or at the individual loci level (e.g., for each of 10 to 20,000 polymorphic loci associated with chromosomes of the set of chromosomes).

Ratios of counts between pairs of chromosomes (e.g., chromosomes 13, 18, and 21) can also be generated in relation to NIPT characterizations of aneuploidy. Ratios of counts can be between chromosomes 13 and 18, chromosomes 18 and 21, chromosomes 13 and 21, and/or other pairs of chromosomes. Ratios of counts can additionally or alternatively be generated between other chromosomes or other loci of interest. As such, the method 100 can include generating a set of values of count ratios between pairs of chromosomes of the set of chromosomes S133, and returning an analytical result based upon the set of values of count ratios S134. In one example, S134 can include returning at least one of an aneuploidy status and a trisomy status for a subject associated with the sample, based upon the count and/or set of values of count ratios.

As indicated above, Step S130 can include generating greater than 50,000 counts per chromosome for each of a set of chromosomes of interest, greater than 60,000 counts per chromosome for each of a set of chromosomes of interest, greater than 70,000 counts per chromosome for each of a set of chromosomes of interest, greater than 80,000 counts per chromosome for each of a set of chromosomes of interest, greater than 90,000 counts per chromosome for each of a set of chromosomes of interest, greater than 100,000 counts per chromosome for each of a set of chromosomes of interest, greater than 120,000 counts per chromosome for each of a set of chromosomes of interest, greater than 130,000 counts per chromosome for each of a set of chromosomes of interest, greater than 140,000 counts per chromosome for each of a set of chromosomes of interest, greater than 150,000 counts per chromosome for each of a set of chromosomes of interest, greater than 160,000 counts per chromosome for each of a set of chromosomes of interest, greater than 170,000 counts per chromosome for each of a set of chromosomes of interest, greater than 180,000 counts per chromosome for each of a set of chromosomes of interest, greater than 190,000 counts per chromosome for each of a set of chromosomes of interest, greater than 200,000 counts per chromosome for each of a set of chromosomes of interest, greater than 210,000 counts per chromosome for each of a set of chromosomes of interest, greater than 220,000 counts per chromosome for each of a set of chromosomes of interest, greater than 230,000 counts per chromosome for each of a set of chromosomes of interest, greater than 240,000 counts per chromosome for each of a set of chromosomes of interest, greater than 250,000 counts per chromosome for each of a set of chromosomes of interest, greater than 260,000 counts per chromosome for each of a set of chromosomes of interest, greater than 270,000 counts per chromosome for each of a set of chromosomes of interest, greater than 280,000 counts per chromosome for each of a set of chromosomes of interest, greater than 290,000 counts per chromosome for each of a set of chromosomes of interest, greater than 300,000 counts per chromosome for each of a set of chromosomes of interest, or even greater counts per chromosome for each of a set of chromosomes of interest.

In relation to Step S130, the method can include returning a characterization of an aneuploidy of a subject associated with the sample S136. Variations of aneuploidies can include sex aneuploidies (e.g., Klinefelter syndrome, Turner syndrome, etc.), trisomies (e.g., Downs syndrome, Edwards syndrome, Palau syndrome, etc.), partial aneuploidies (e.g., Robertsonian translocations), monosomies, and/or other genetic conditions that can be determined based upon generated counts and/or count ratios.

In relation to Step S130, the method can additionally or alternatively include: returning a characterization of relative abundances of targets, based upon the set of counts S135. Relative abundances characterized can include relative abundances of alleles of SNPs of the set of chromosomes, to generate an estimate of fetal fraction (FF) in the sample. The estimate of FF can then be used to enable determinations of conclusiveness of NIPT results.

In variations, SNP alleles processed and evaluated in Step S135 to determine FF can include SNPs associated with chromosomes 1, 13, 18, 21, X, and/or Y, at various loci (e.g., from 10 to 20,000 polymorphic loci); however, SNPs characterized to determine FF can additionally or alternatively be associated with other chromosomes and/or loci. SNPs evaluated can be biallelic or multiallelic, with more than two alleles per SNP. SNPs evaluated can further be characterized by a high minor allele fraction (MAF), with an MAF above a suitable threshold (e.g., MAF>0.2, MAF>0.3, MAF>0.4, etc.); however, SNPs evaluated can be characterized with other MAF values. SNPs evaluated can be for coding regions (e.g., synonymous, non-synonymous, missense, nonsense) and/or non-coding regions.

With respect to determination of FF in Step S135, target panels undergoing evaluation can be designed such that FF associated with fetus of any gender can be determined, without requiring detection of chromosome Y markers. As such, for a male fetus, FF can be estimated by the amount of chromosome Y fragments present in the sample (e.g., maternal sample) relative to the amount of other non-sex chromosomes. For determination of FF for a female fetus, the set of SNPs evaluated are selected such that for each fetus-mother pair, there would be at least a few SNPs in the common SNP panel that are homozygous in mother and heterozygous in fetus. The count of the alternate allele from the fetus, when compared to the count of the homozygous allele (from mother, and also half from fetus), would yield FF for a female fetus (or non-male fetus, such as in intersex conditions).

In a specific application, Step S135 can implement counting requirements per reference chromosome to provide indications of confidence in NIPT assay results with respect to threshold FF values. In a specific example, for a counting requirement of 400,000 counts per reference chromosome, the lowest FF (e.g., DNA FF) in which an anueploidy assay would be confident in calling a true negative is ~4%; thus, the FF assay estimates <4% DNA FF, then the results from the aneuploidy assay would be inconclusive. However, if the FF assay estimates>4% DNA FF, then the results from the aneuploidy assay would be more conclusive with increasing FF.

However, in other specific examples, the counting requirement per reference chromosome can be set at another value (e.g., less than 400,000 counts, greater than 400,000 counts, etc.) in relation to other FF threshold values (e.g., 3%, 5%, 6%, other percentages, etc.).

2.4 Example

Figure 5:
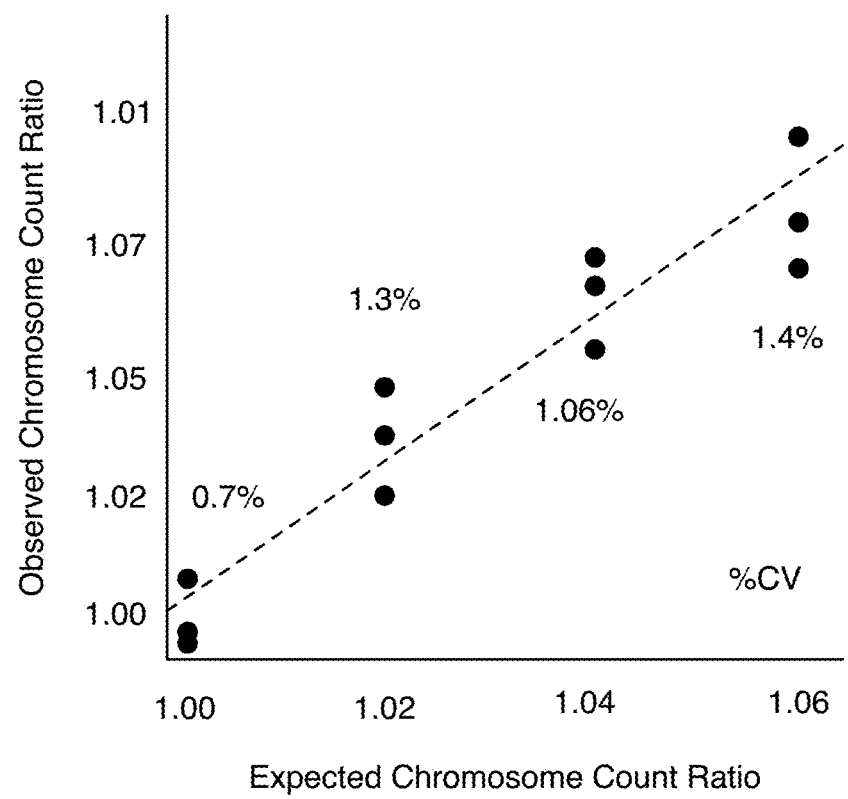
FIG. 5 depicts example results comparing observed and expected chromosome count ratios.

Example: In an example, each of the chromosomes 13, 18, and 21 were targeted with a chromosome-specific probe that was conjugated with a different fluorophore and compatible with detection capabilities of an optical detection system (e.g., a multi-color lightsheet 3D imager). In the example, in silico primer design was used to identify over 100 primer pairs per chromosome with low probability for non-specific primer interaction. From this primer pool, the platform implemented a group of primers (e.g., primer panels with over 70-plex capability for each chromosome, other primer panels having capabilities for multiplexing described) that amplify a desired number of loci per chromosome (e.g., over 70 loci per chromosome) to achieve a desired number of counts from a typical blood draw (e.g., 10 mL) from expectant mothers. Using this pilot digital ultraPCR assay, the platform demonstrated results confirming that the digital PCR assay with ultra partitioning (ultraPCR) can differentiate different % FF by comparing DNA counts from chromosomes 21 and 18, using a 6.25 ng DNA input that is equivalent to 25% of a 10 mL blood draw (as shown in FIG. 5). Even at feasibility stage, this multicolor multiplex (e.g., over 70-plex) assay (e.g., over 210 plex) produces significantly improved results for NIPT in a non-NGS setting.

In variations primers can be designed to target regions outside of common CNVs and SNPs, and with minimal interaction with probes and other primers in the panel. Each individual assay was tested on genomic DNA samples to ensure it produced the correct chromosomal ratios before combining into final primer panels.

Further embodiments of the platform involve architecture suited for use in clinical and commercial settings, where TABLE 1 includes example achievable specifications of the NIPT ultraPCR assay and platform specifications for ultraPCR in order to support a NIPT workflow (e.g., in a decentralized laboratory setting).

4. Computer Systems

Figure 6:
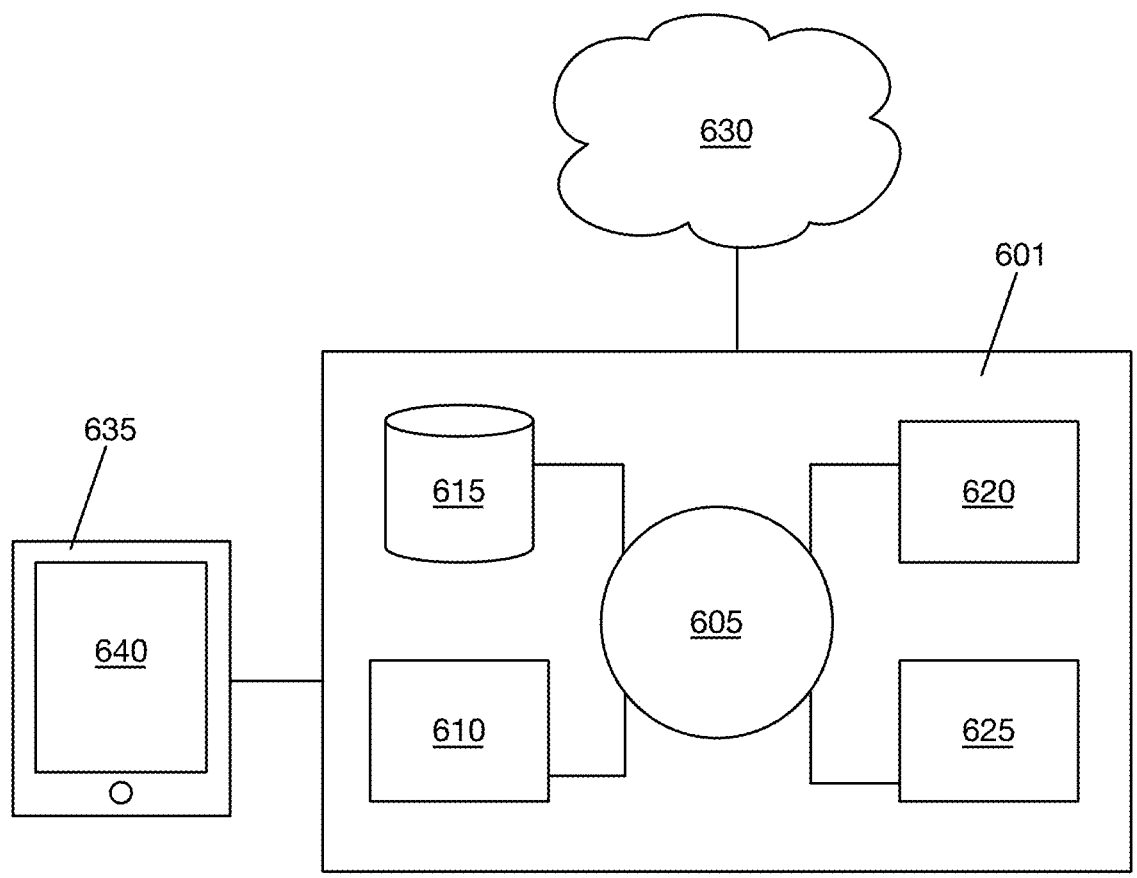
FIG. 6 illustrates a computer system that is programmed or otherwise configured to implement methods provided herein.

The present disclosure provides computer systems that are programmed to implement methods of the disclosure. FIG. 6 shows a computer system 601 that is programmed or otherwise configured to, for example, perform a non-invasive prenatal testing (NIPT) digital assay upon generating at least a large number of counts per chromosome for a set of

TABLE 1

Example Specifications for NIPT ultraPCR assay and ultraPCR platform.

| ID | Category | Specification | Level 1 Performance | Level 2 Performance |
|---|---|---|---|---|
| 1 | NIPT ultraPCR | Intended Use | Quantitative system used to detect fetal trisomy from maternal blood sample at 10 weeks gestation. | |
| 2 | | Specimen type | cfDNA isolated from plasma | |
| 3 | | Sample input requirements | 1 10 mL blood draw, 25 ng cfDNA | 2 10 mL blood draws, 50 ng cfDNA |
| 4 | | % FF with >99% sensitivity and specificity | 4% | 6% |
| 5 | | Number of chromosomes interrogated per sample tube | 5, chromosomes, 13, 18, 21, X, and Y | 3, chromosomes 13, 18, and 21 for tube 1, and chromosomes X and Y tube 2. |
| 6 | | Total workflow time after cfDNA extraction | 3 hours | 6 hours |
| 7 | ultraPCR Platform | Reaction volume | 50 uL | |
| 8 | | Dead volume of system | <5% | <10% |
| 9 | | % CV for high order DNA counting | <2% | <3% |
| 10 | | Colors supported | at least 5 | at least 4 |
| 11 | | Interpretation of results | Software provided to count DNA molecules after 3D lightsheet scanning with graphic user interface. | |
| 12 | | Instrument usage | Fully-dry with sample lids closed to avoid cross-contamination | |
| 13 | | Consumable usage | Single-use, disposable | |
| 14 | | Consumable sterilization | DNA-free & DNase-free | |
| 15 | | Shipping conditions | PCR reagents with cold gel packs Emulsion reagents and consumables in ambient temperature | |
| 16 | | Storage conditions | PCR reagents in −20 C. Emulsion reagents and consumables in ambient temperature | |
| 17 | | Reagent and consumable shelf life | 24 months | 12 months |
| 18 | | Training | Laboratory technicians can be proficient with one week of hands-on training. | |

TABLE 2

Example results of an NIPT ultraPCR assay

| % Trisomy 21 | Metric | Chr13 Counts | Chr21 Counts | Chr18 Counts | Chr21/13 Ratio | Chr21/18 Ratio | Chr13/18 Ratio |
|---|---|---|---|---|---|---|---|
| 0 | Mean | 272589 | 284675 | 270602 | 1.044 | 1.052 | 1.007 |
| | (% CV) | (2.798%) | (2.644%) | (2.696%) | (0.343%) | (0.377%) | (0.319%) |
| 4 | Mean | 276641 | 293851 | 273524 | 1.062 | 1.074 | 1.011 |
| | (% CV) | (3.070%) | (3.210%) | (3.089%) | (0.393%) | (0.378%) | (0.397%) |
| 6 | Mean | 262783 | 281465 | 259506 | 1.071 | 1.085 | 1.013 |
| | (% CV) | (3.630%) | (3.811%) | (3.777%) | (0.402%) | (0.532%) | (0.647%) |
| 10 | Mean | 266260 | 289984 | 263157 | 1.089 | 1.102 | 1.012 |
| | (% CV) | (2.591%) | (2.808%) | (2.692%) | (0.456%) | (0.403%) | (0.359%) | chromosomes present in a sample, where performing the NIPT digital assay can include: simultaneously distributing a) nucleic acids of the sample, said nucleic acids comprising target loci of the set of chromosomes, and b) materials for an amplification reaction across a plurality of partitions; amplifying said nucleic acids with said materials for the amplification reaction, within the plurality of partitions; and generating said counts per chromosome upon detecting signals from the plurality of partitions. The computer system 601 can additionally or alternatively perform other aspects of NIPT digital assays for characterization of an aneuploidy in a subject, and/or perform other suitable digital assays involving other loci of interest.

The computer system 601 can regulate various aspects of analysis, calculation, and generation of the present disclosure, such as, for example, generating a plurality of partitions (e.g., from an aqueous mixture including sample material and materials for an amplification reaction) within a collecting container at a desired rate, transmitting heat to and from the plurality of partitions within the collecting container, performing an optical interrogation operation with the plurality of partitions within the collecting container, and/or performing one or more NIPT or other assay steps. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet.

In some embodiments, the network 630 is a telecommunication and/or data network. The network 630 can include one or more computer servers, which can enable distributed computing, such as cloud computing. For example, one or more computer servers may enable cloud computing over the network 630 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 630, with the aid of the computer system 601, can implement a peer-to-peer network, which may enable devices coupled to the computer system 101 to behave as a client or a server.

The CPU 605 may comprise one or more computer processors and/or one or more graphics processing units (GPUs). The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some embodiments, the circuit is an application specific integrated circuit (ASIC).

The storage unit 615 can store files, such as drivers, libraries and saved programs. The storage unit 615 can store user data, e.g., user preferences and user programs. In some embodiments, the computer system 601 can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 1115. The machine executable or machine readable code can be provided in the form of software. During use, the code can be executed by the processor 605. In some embodiments, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Embodiments of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, a visual display indicative of performing a non-invasive prenatal testing (NIPT) digital assay upon generating at least a large number of counts per chromosome for a set of chromosomes present in a sample, where performing the NIPT digital assay can include: simultaneously distributing a) nucleic acids of the sample, said nucleic acids comprising target loci of the set of chromosomes, and b) materials for an amplification reaction across a plurality of partitions; amplifying said nucleic acids with said materials for the amplification reaction, within the plurality of partitions; and generating said counts per chromosome upon detecting signals from the plurality of partitions. The UI 640 can additionally or alternatively be adapted for performing other digital assays involving other loci of interests and/or other calculations, as described. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, generate a plurality of droplets within a collecting container with desired characteristics.

5. Conclusions

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or, if applicable, portion of code, which comprises one or more executable instructions for implementing the specified logical function (s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for performing a non-invasive prenatal testing (NIPT) digital assay, the method comprising:
    (a) obtaining a nucleic acid sample comprising a plurality of target nucleic acid molecules, wherein said plurality of target nucleic acid molecules comprises sequences associated with a plurality of chromosomes;
    (b) generating a plurality of partitions, wherein said plurality of partitions comprises at least 9 million partitions, and wherein each partition of said plurality of partitions comprises:
        (i) materials for an amplification reaction; and
        (ii) less than or equal to one target nucleic acid molecule of said plurality of target nucleic acid molecules, wherein each target nucleic acid molecule comprises a sequence corresponding to a chromosome;
    (c) amplifying said plurality of target nucleic acid molecules within said plurality of partitions; and
    (d) detecting signals from said plurality of partitions, thereby generating counts corresponding to said plurality of chromosomes, wherein at least 150,000 counts are generated for each chromosome of said plurality of chromosomes.

2. The method of claim 1, wherein less than 6% of nucleic acid molecules of said nucleic acid sample are of fetal origin.

3. The method of claim 1, wherein said plurality of chromosomes comprises chromosome 21.

4. The method of claim 1, wherein said plurality of chromosomes comprises chromosome 18.

5. The method of claim 1, wherein said plurality of chromosomes comprises chromosome 13.

6. The method of claim 1, wherein said materials for an amplification reaction comprise primers configured to amplify at least 70 loci of a chromosome of said plurality of chromosomes.

7. The method of claim 1, wherein said plurality of target nucleic acid molecules comprise at least 210 different target loci.

8. The method of claim 1, wherein said nucleic acid sample comprises nucleic acid molecules extracted from plasma.

9. The method of claim 1, wherein less than 15% of partitions of said plurality of partitions comprise one target nucleic acid molecule.

10. The method of claim 9, wherein less than 10% of partitions of said plurality of partitions comprise one target nucleic acid molecule.

11. The method of claim 1, wherein (b) comprises centrifuging said nucleic acid sample through a substrate having a distribution of holes.

12. The method of claim 1, wherein said plurality of partitions is contained within a collecting container and wherein (d) comprises scanning a set of cross sections of a collecting container containing the plurality of partitions.

13. The method of claim 1, wherein (c) and (d) is completed within a duration of no more than 3 hours.

14. The method of claim 1, wherein said plurality of partitions comprises at least 25 million partitions.

15. The method of claim 1, wherein (d) comprises generating at least 200,000 counts per chromosome for each of the plurality of chromosomes.

16. The method of claim 1, wherein said plurality of chromosomes comprises chromosome X.

17. The method of claim 1, wherein said plurality of chromosomes comprises chromosome Y.

* * * * *